United States Patent
Turner, Jr. et al.

(10) Patent No.: US 7,144,730 B2
(45) Date of Patent: *Dec. 5, 2006

(54) LIPOXYGENASE PROTEINS AND POLYNUCLEOTIDES ENCODING THE SAME

(75) Inventors: C. Alexander Turner, Jr., The Woodlands, TX (US); Brian Zambrowicz, The Woodlands, TX (US); Michael Nehls, Stockdorf (DE); Glenn Friedrich, Houston, TX (US); Arthur T. Sands, The Woodlands, TX (US)

(73) Assignee: Lexicon Genetics Incorporated, The Woodlands, TX (US)

( * ) Notice: Subject to any disclaimer, the term of this patent is extended or adjusted under 35 U.S.C. 154(b) by 346 days.

This patent is subject to a terminal disclaimer.

(21) Appl. No.: 10/422,264

(22) Filed: Apr. 23, 2003

(65) Prior Publication Data

US 2003/0172391 A1    Sep. 11, 2003

Related U.S. Application Data

(62) Division of application No. 09/547,435, filed on Apr. 12, 2000, now Pat. No. 6,582,957.

(60) Provisional application No. 60/150,454, filed on Aug. 24, 1999, provisional application No. 60/128,817, filed on Apr. 12, 1999.

(51) Int. Cl.
*C12N 5/10* (2006.01)
*C12N 15/85* (2006.01)
*C12N 15/70* (2006.01)
*C07H 21/04* (2006.01)

(52) U.S. Cl. .................... 435/325; 536/23.1; 536/23.2; 536/23.5; 435/320.1; 424/93.7

(58) Field of Classification Search ...................... None
See application file for complete search history.

(56) References Cited

U.S. PATENT DOCUMENTS 6,204,037 B1    3/2001    Brash et al.

FOREIGN PATENT DOCUMENTS

| EP | 0 325 773 A1 | 8/1989 |
|----|--------------|--------|
| WO | WO 94/05777 | 3/1994 |
| WO | WO 99/13111 | 3/1999 |

OTHER PUBLICATIONS

Entrez Nucleotide Database entry accession No. AF059250.1.*
Entrez Nucleotide Database entry accession No. AF038461.1.*
Entrez Nucleotide Database entry accession No. U78294.1.*
Boeglin et al. A 12R-lipoxygenase in human skin: mechanistic evidence, molecular cloning, and expression. Proc Natl Acad Sci U S A. Jun. 9, 1998;95(12):6744-9.*

Brash et al. Discovery of a second 15S-lipoxygenase in humans. Proc Natl Acad Sci U S A. Jun. 10, 1997;94(12):6148-52.*

Sun et al. Human 12(R)-lipoxygenase and the mouse ortholog. Molecular cloning, expression, and gene chromosomal assignment. J Biol Chem. Dec. 11, 1998;273(50):33540-7.*

Kean et al. Interactions of oligonucleotide analogs containing methylphosphonate internucleotide linkages and 2'-O-methylribonucleosides. Nucleic Acids Res. Oct. 25, 1994;22(21):4497-503.*

Panjkovich et al. Comparison of different melting temperature calculation methods for short DNA sequences. Bioinformatics. Mar.2005;21(6):711-22.*

Boado et al., "Differential expression of arachidonate 5-lipoxygenaes transcripts in human brain tumors: Evidence for the expression of a multitranscript family," *Proc. Natl. Acad. Sci. USA*, 89:9044-9048 (1992).

Boeglin et al., "A 12R-lipoxygenase in human skin: Mechanistic evidence, molecular cloning, and expression," *Proc. Natl. Acad. Sci. USA*, 95:6744-6749 (1998).

Bork, "Powers and pitfalls in sequence analysis: The 70% hurdle," *Genomic Research*, 10: 398-400 (2000).

Bork, "Go hunting in sequence databases but watch out for the traps," *TIG*, 12:425-427 (1996).

Bork, "Protein annotation: detective work for function prediction," *TIG*, 14:248-250 (1998).

Brash et al., "Discovery of a second 15S-lipoxygenase in humans," *Proc. Natl. Acad. Sci. USA*, 94:6148-6152 (1997).

Brenner, "Errors in genome annotation," *TIG*, 15:132-133 (1999).

Marshall, "Gene therapy's growing pains," *Science*, 269:1050-1055 (1995).

Orkin et al., "Report and recommendations of the panel to assess the NIH investment in research on gene therapy," (1995). Available through N.I.H. and at http://www.nih.gov/news/panelrep/.

Ross et al., "Gene therapy in the United states: A five-year status report," *Human Gene Therapy*, 7:1781-1790 (1996).

Rouzer et al., "Characterization of cloned human leukocyte 5-lipoxygenase expressed in mammalian cells," *Journal of Biological Chemistry*, 263:10135-10140 (1988).

Skolnick et al., "From genes to protein structure and function: novel applications of computational approaches in the genomic era," *Trends in Biotech*, 18:34-39 (2000).

Smith et al., "The challenges of genome sequence annotation or 'The devil is in the details'," *Nature Biotechnology*, 15:1222-1223 (1997).

(Continued)

*Primary Examiner*—Daniel M. Sullivan
(74) *Attorney, Agent, or Firm*—Finnegan, Henderson, Farabow, Garrett & Dunner, LLP

(57) ABSTRACT

The nucleotide and corresponding amino acid sequences are reported for a novel class of mammalian lipoxygenase proteins. The novel lipoxygenase encoding polynucleotides were obtained from human gene trap clones and human cDNA libraries.

3 Claims, No Drawings

OTHER PUBLICATIONS

Sun et al., "Human 12(R)-lipoxygenase and the mouse ortholog," *The Journal of Biological Chemistry*, 273:33540-33547 (1998).

Verma et al., "Gene therapy-promises, problems and prospects," *Nature*, 389:239-242 (1997).

* cited by examiner

LIPOXYGENASE PROTEINS AND POLYNUCLEOTIDES ENCODING THE SAME

This application is a divisional of U.S. patent application Ser. No. 09/547,435, filed Apr. 12, 2000, now U.S. Pat. No. 6,582,957, which claims priority to U.S. Provisional Application Nos. 60/128,817, filed Apr. 12, 1999, and 60/150,454, filed Aug. 24, 1999. The entire contents of U.S. patent application Ser. No. 09/547,435 are incorporated herein by reference in its entirety for any purpose.

1. INTRODUCTION

The present invention relates to the discovery, identification, and characterization of novel human polynucleotides that encode proteins that share sequence similarity with lipoxygenases. The invention encompasses the described polynucleotides, host cell expression systems, the encoded proteins, fusion proteins, polypeptides and peptides, antibodies to the encoded proteins and peptides, and genetically engineered animals that lack the disclosed genes or overexpress the disclosed genes, or antagonists and agonists of the proteins, and other compounds that modulate the expression or activity of the proteins encoded by the disclosed polynucleotides that can be used for diagnosis, drug screening, clinical trial monitoring, or the treatment of physiological or behavioral disorders.

2. BACKGROUND OF THE INVENTION

Lipoxygenases are enzymes that mediate the oxidation of lipid substrates. As such, lipoxygenases are involved in the synthesis of leukotrienes. Leukotrienes influence a variety of biological processes, and can serve as, inter alia, potent chemotactic agents, and mediators of inflammation, smooth muscle contraction, etc. Accordingly, lipoxygenases represent a key target for the regulation of a variety of biological pathways and conditions.

3. SUMMARY OF THE INVENTION

The present invention relates to the discovery, identification, and characterization of nucleotides that encode novel human lipoxygenase proteins, and the corresponding amino acid sequences of these proteins. The novel human proteins (NHPs) described for the first time herein share structural similarity with animal and plant lipoxygenase proteins. As such, the novel genes represent a new class of lipoxygenase proteins with a range of homologues and orthologs that transcend a broad range of phyla and species.

The invention comprises (a) polypeptides with SEQ ID NOS:2, 4, 6, 8, 10, 12, 14, 16, 18, 20, 22, 24, 26, and 28; (b) homologues and allelic variants of SEQ ID NOS:2, 4, 6, 8, 10, 12, 14, 16, 18, 20, 22, 24, 26, and 28; (c) fragments of SEQ ID NOS:2, 4, 6, 8, 10, 12, 14, 16, 18, 20, 22, 24, 26, and 28 of any size, for example, from 4 amino acids to less than the full-length of a polypeptide of SEQ ID NOS:2, 4, 6, 8, 10, 12, 14, 16, 18, 20, 22, 24, 26, or 28 and any number between; (d) fragments of SEQ ID NOS:2, 4, 6, 8, 10, 12, 14, 16, 18, 20, 22, 24, 26, and 28 that correspond to a functional domain (for example, a catalytic domain, a signal sequence, a ligand binding domain, a regulatory domain, etc.); (e) fusion proteins comprising a polypeptide sequence of any one of (a) through (d); (f) mutant polypeptides (including engineered and naturally occurring mutants) comprising a polypeptide sequence of any one of (a) through (d), including, but not limited to, deletion mutants, insertion mutants, substitution mutants, and mutant polypeptides in which all or a part of at least one of the domains is deleted or altered (e.g., a mutant of the active site with altered substrate specificity).

The invention further comprises (g) polynucleotides with SEQ ID NOS:1, 3, 5, 7, 9, 11, 13, 15, 17, 19, 21, 23, 25, 27, and 29; (h) polynucleotides encoding any one of the polypeptides of the invention including, but not limited to, polypeptides specifically described in (a) through (f) above; (i) polynucleotides capable of hybridizing to a second polynucleotide that is complementary to a polynucleotide described in (g) and/or (h) above under conditions of low, medium, or high stringency; (j) oligonucleotides corresponding to a segment of a polynucleotide described in (g) through (i) above and such oligonucleotides having any size from 2 nucleotides through less than the full-length polynucleotide and any length inbetween.

In certain embodiments, the novel human nucleic acid sequences described herein, encode proteins/open reading frames (ORFs) of 711, 489, 556, 334, 615, 460, 291, 69, 139, 195, 110, 867, 645, and 771 amino acids in length (see SEQ ID NOS:2, 4, 6, 8, 10, 12, 14, 16, 18, 20, 22, 24, 26, and 28 respectively).

The invention further comprises antibodies to any one of the polypeptides or polynucleotides of the invention. The invention also comprises host cells that are engineered to contain and/or express any one of the polynucleotides and/or polypeptides of the invention.

The invention also comprises agonists and antagonists of the described NHPs, including small molecules, large molecules, mutant NHPs, or portions thereof that compete with native NHP, and antibodies. The invention further comprises nucleotide sequences that can be used to inhibit the expression of the described NHPs (e.g., antisense and ribozyme oligonucleotides and/or polynucleotides, and gene or regulatory sequence replacement constructs) or to enhance the expression of the described NHP genes (e.g., expression constructs that place the described gene under the control of a strong promoter system), and transgenic animals that express a NHP transgene, or "knock-outs" (which can be conditional) that do not express functional NHP.

Further, the present invention also relates to methods for identifying compounds that modulate, i.e., act as agonists or antagonists of, NHP expression and/or NHP product activity that utilize purified preparations of the described NHPs and/or NHP product, or cells expressing the same. Such compounds can be used as therapeutic agents for the treatment of any of a wide variety of symptoms associated with biological disorders or imbalances.

4. DESCRIPTION OF THE SEQUENCE LISTING AND FIGURES

The Sequence Listing provides the sequences of 14 lipoxygenase-like ORFs that are encoded by the described NHP polynucleotides (SEQ ID NOS:1, 3, 5, 7, 9, 11, 13, 15, 17, 19, 21, 23, 25, 27, and 29) and the amino acid sequences (SEQ ID NOS:2, 4, 6, 8, 10, 12, 14, 16, 18, 20, 22, 24, 26, and 28) encoded thereby.

5. DETAILED DESCRIPTION OF THE INVENTION

Lipoxygenases oxidize, or oxygenate, lipids to produce leukotrienes. Depending on the leukotriene synthesized, a wide variety of biological functions can be affected. Typically, leukotrienes will bind cognate receptors an trigger a biological effect (such as, for example, signal transduction). Interfering with lipoxygenase activity ultimately effects leukotriene production and downstream leukotriene-mediated processes. Alternatively, enhancing lipoxygenase activity in vivo, can boost the effects/activity levels the corresponding biological processes. Various lipoxygenase activities can be found in a variety of cells and tissues in both animals and plants. Three predominant types of lipoxygenases include the 5-, 12-, and 15-lipoxygenases, and each type of lipoxygenase can have additional forms depending upon the tissues or cells in which they are expressed.

The 5-, 12-, and 15-lipoxygenases, and the leukotrienes they produce, have been implicated with a variety of diseases and disorders. Given that leukotrienes can modulate inflammatory reactions, they have been associated with a spectrum of mammalian diseases including, but not limited to, asthma, eye diseases, anaphylaxis, lung disease, hematological disorders, infectious diseases, granulomatosis, abscess, pacreatitis, prostatitis, hepatitis, atherosclerosis, heart disease, graft rejection, thrombosis, restenosis, ulcers, kidney disease, hypertension, dermatoses, cramping, autoimmune disorders (lupus, scleroderma, Crohn's disease, rheumatoid arthritis, etc.), granulomatosis, hyperproliferative diseases, cancer, nausea, headache, metastases, inflammatory bowel disorder, allergy, cancer, arthritis, eczema, melanoma, erythema, acne, psoriasis, shingles, infectious disease, and diabetes. Accordingly, one embodiment of the present invention are processes for identifying compounds useful for the treatment of one or more of the above diseases and disorders that include the use of one or more of the described lipoxygenase-like genes, proteins, or a novel portion thereof.

Given the biological importance of lipoxygenases, the genes encoding such proteins (and the proteins encoded thereby as well as inhibitors thereof) have been subjected to intense scientific/commercial scrutiny (see, for example, U.S. Pat. Nos. 5,036,105, 5,162,365, 5,504,097, 5,066,679, 5,830,453, 4,761,403, 5,589,506, 5,026,729, and 5,861,268) (all of which are herein incorporated by reference in their entirety).

The presently described NHPs share significant similarity with previously described human lipoxygenases. Expression studies using RT-PCR detect NHP transcripts in, inter alia, neural tissue (i.e., brain, spinal cord, etc.), skin, testis, prostate, adrenal gland, cervix, salivary gland, pancreas, heart, lymphoid cells (lymph node, spleen, thymus), and mammary glands. Northern analysis showed a predominant signal in testis, with less predominant, but longer, transcripts detectable in testis, lymph node, and spinal cord. A full length cDNA of a NHP coding region (with 5' and 3' extensions) was isolated from a human brain cDNA library (Edge BioSystems, Gaithersburg, Md.) and sequenced (SEQ ID NO: 29). A possible murine ortholog of the described NHPs is predominantly expressed in skin (Kinzig et al., 1999, Genomics 58:158–164).

The invention encompasses the use of the described NHP nucleotides, NHPs and peptides, as well as antibodies, preferably monoclonal antibodies, or binding fragments, domains, or fusion proteins thereof, or anti-idiotypic variants derived therefrom, that bind NHPs, other antagonists that inhibit binding activity or expression, or agonists that activate NHP activity or increase NHP expression, in the diagnosis and/or treatment of disease.

In particular, the invention described in the subsections below encompasses NHP polypeptides or peptides corresponding to functional domains of NHPs, mutated, truncated or deleted NHPs (e.g., NHPs missing one or more functional domains or portions thereof), NHP fusion proteins (e.g., a NHP or a functional domain of a NHP fused to an unrelated protein or peptide such as an immunoglobulin constant region, i.e., IgFc), nucleotide sequences encoding such products, and host cell expression systems that can produce such NHP products.

The invention also encompasses antibodies and anti-idiotypic antibodies (including Fab fragments), antagonists and agonists of the NHP, as well as compounds or nucleotide constructs that inhibit expression of a NHP gene (transcription factor inhibitors, antisense and ribozyme molecules, or gene or regulatory sequence replacement constructs), or promote expression of NHP (e.g., expression constructs in which NHP coding sequences are operatively associated with expression control elements such as promoters, promoter/enhancers, etc.). The invention also relates to host cells and animals genetically engineered to express the NHPs (or mutant variants thereof) or to inhibit or "knock-out" expression of an animal homolog of an endogenous NHP gene.

The NHPs or peptides, NHP fusion proteins, NHP nucleotide sequences, antibodies, antagonists and agonists can be useful for the detection of mutant NHPs or inappropriately expressed NHPs for the diagnosis of disease. The NHP proteins or peptides, NHP fusion proteins, NHP nucleotide sequences, host cell expression systems, antibodies, antagonists, agonists and genetically engineered cells and animals can be used for screening for drugs (or high throughput screening of combinatorial libraries) effective in the treatment of the symptomatic or phenotypic manifestations of perturbing the normal function of NHP in the body.

The use of engineered host cells and/or animals offers an advantage in that such systems allow for both the identification of compounds that interact with an NHP, and also provide information regarding the biological significance of the NHP.

Finally, NHP products (especially soluble derivatives such as peptides corresponding to the NHP), and NHP fusion protein products (such as NHP-Ig fusion proteins, i.e., fusions of a NHP, or a domain of a NHP, to an IgFc), antibodies and anti-idiotypic antibodies (including Fab fragments), antagonists or agonists (including compounds that modulate signal transduction which may act on downstream targets in a NHP-associated leukotriene pathway) can be used to directly treat diseases or disorders.

Nucleotide constructs encoding such NHP products can be delivered to host cells that subsequently express the products in vivo; these genetically engineered cells function as "bioreactors" in the body delivering a continuous supply of a NHP, a NHP peptide, or a NHP fusion protein to the body. Nucleotide constructs encoding functional NHPs, mutant NHPs, as well as antisense and ribozyme molecules can also be used in "gene therapy" approaches for the modulation of NHP expression. Thus, the invention also encompasses pharmaceutical formulations and methods for treating biological disorders.

Various aspects of the invention are described in greater detail in the subsections below.

5.1. NHP Polynucleotides

The cDNA sequences (SEQ ID NOS: 1, 3, 5, 7, 9, 11, 13, 15, 17, 19, 21, 23, 25, 27, and 29) and deduced amino acid sequences (SEQ ID NOS: 2, 4, 6, 8, 10, 12, 14, 16, 18, 20, 22, 24, 26, and 28) corresponding to the described NHPs are presented in the Sequence Listing. The NHP ORFs were obtained from human testis and brain cDNA libraries using probes and/or primers generated from human gene trapped sequence tags.

The NHP sequences of the present invention include: (a) the human DNA sequences presented in the Sequence Listing and additionally contemplate any nucleotide sequence encoding a contiguous and functional NHP that hybridizes to a complement of the DNA sequences presented in the Sequence Listing under highly stringent conditions, e.g., hybridization to filter-bound DNA in 0.5 M NaHPO$_4$, 7% sodium dodecyl sulfate (SDS), 1 mM EDTA at 65° C., and washing in 0.1×SSC/0.1% SDS at 68° C. (Ausubel F. M. et al., eds., 1989, Current Protocols in Molecular Biology, Vol. I, Green Publishing Associates, Inc., and John Wiley & sons, Inc., New York, at p. 2.10.3) and encodes a functionally equivalent gene product. Additionally contemplated are any nucleotide sequences that hybridize to the complement of the DNA sequences that encode and express an amino acid sequence presented in the Sequence Listing under moderately stringent conditions, e.g., washing in 0.2×SSC/0.1% SDS at 42° C. (Ausubel et al., 1989, supra), yet which still encode a functionally equivalent NHP product. Functional equivalents of NHP include naturally occurring NHPs present in other species, and mutant NHPs whether naturally occurring or engineered. The invention also includes degenerate variants of the disclosed sequences.

The invention also includes nucleic acid molecules, preferably DNA molecules, that hybridize to, and are therefore the complements of, the described NHP nucleotide sequences. Such hybridization conditions may be highly stringent or less highly stringent, as described above. In instances wherein the nucleic acid molecules are deoxyoligonucleotides ("DNA oligos"), such molecules (and particularly about 16 to about 100 base long, about 20 to about 80, or about 34 to about 45 base long, or any variation or combination of sizes represented therein that incorporate a contiguous region of sequence first disclosed in the present Sequence Listing, can be used in conjunction with the polymerase chain reaction (PCR) to screen libraries, isolate clones, and prepare cloning and sequencing templates, etc.

Alternatively, the oligonucleotides can be used singly or in chip format as hybridization probes. For example, a series of the described NHP oligonucleotide sequences, or the complements thereof, can be used to represent all or a portion of the described NHP sequences. The oligonucleotides, typically between about 16 to about 40 (or any whole number within the stated range) nucleotides in length, may partially overlap each other and/or the NHP sequence may be represented using oligonucleotides that do not overlap. Accordingly, the described NHP polynucleotide sequences shall typically comprise at least about two or three distinct oligonucleotide sequences of at least about 18, and preferably about 25, nucleotides in length that are first disclosed in the described Sequence Listing. Such oligonucleotide sequences may begin at any nucleotide present within a sequence in the Sequence Listing and proceed in either a sense (5'-to-3') orientation vis-a-vis the described sequence or in an antisense orientation. For oligonucleotide probes, highly stringent conditions may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may encode or act as NHP gene antisense molecules, useful, for example, in NHP gene regulation (for and/or as antisense primers in amplification reactions of NHP gene nucleic acid sequences). With respect to NHP gene regulation, such techniques can be used to regulate biological functions. For example, it has been reported that lipoxygenase mRNA can be translationally "silenced" by a differentiation control element in the 3' untranslated region (UTR) of the transcript in erythroid cells (Ostareck et al., 1997, Cell, 89:597–606). Further, such sequences may be used as part of ribozyme and/or triple helix sequences, also useful for NHP gene regulation.

Lipoxygenase antisense oligonucleotides may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

The antisense oligonucleotide may also comprise at least one modified sugar moiety selected from the group including, but not limited to, arabinose, 2-fluoroarabinose, xylulose, and hexose.

In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641). The oligonucleotide is a 2'-0-methylribonucleotide (Inoue et al., 1987, Nucl. Acids Res. 15:6131–6148), or a chimeric RNA-DNA analogue (Inoue et al., 1987, FEBS Lett. 215:327–330).

Oligonucleotides of the present invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate oligonucleotides can be prepared by use of controlled pore glass polymer supports (Sarin et al., 1988, Proc. Natl. Acad. Sci. U.S.A. 85:7448–7451), etc.

Low stringency conditions are well known to those of skill in the art, and will vary predictably depending on the specific organisms from which the library and the labeled sequences are derived. For guidance regarding such conditions see, for example, Sambrook et al., 1989, Molecular Cloning, A Laboratory Manual (and periodic updates thereof), Cold Springs Harbor Press, N.Y.; and Ausubel et al., 1989, Current Protocols in Molecular Biology, Green Publishing Associates and Wiley Interscience, N.Y.

Alternatively, suitably labeled NHP nucleotide probes may be used to screen a human genomic library using appropriately stringent conditions, or by PCR. The identification and characterization of human genomic clones is helpful for identifying polymorphisms, determining the genomic structure of a given locus/allele, and designing diagnostic tests. For example, sequences derived from regions adjacent to the intron/exon boundaries of the human gene can be used to design primers for use in amplification assays to detect mutations within the exons, introns, splice sites (e.g., splice acceptor and/or donor sites), etc., that can be used in diagnostics and pharmacogenomics.

Further, a NHP gene homolog may be isolated from nucleic acid of the organism of interest by performing PCR using two degenerate oligonucleotide primer pools designed on the basis of amino acid sequences within the NHP product disclosed herein. The template for the reaction may be total RNA, mRNA, and/or cDNA obtained by reverse transcription of mRNA prepared from, for example, human or non-human cell lines or tissue, such as choroid plexus, known or suspected to express a NHP gene allele.

The PCR product may be subcloned and sequenced to ensure that the amplified sequences represent the sequence of the desired NHP gene. The PCR fragment may then be used to isolate a full length cDNA clone by a variety of methods. For example, the amplified fragment may be labeled and used to screen a cDNA library, such as a bacteriophage cDNA library. Alternatively, the labeled fragment may be used to isolate genomic clones via the screening of a genomic library.

PCR technology may also be utilized to isolate full length cDNA sequences. For example, RNA may be isolated, following standard procedures, from an appropriate cellular or tissue source (i.e., one known, or suspected, to express a NHP gene, such as, for example, skin, testis, or brain tissue). A reverse transcription (RT) reaction may be performed on the RNA using an oligonucleotide primer specific for the most 5' end of the amplified fragment for the priming of first strand synthesis. The resulting RNA/DNA hybrid may then be "tailed" using a standard terminal transferase reaction, the hybrid may be digested with RNase H, and second strand synthesis may then be primed with a complementary primer. Thus, cDNA sequences upstream of the amplified fragment may easily be isolated. For a review of cloning strategies which may be used, see e.g., Sambrook et al., 1989, supra.

A cDNA of a mutant NHP gene may be isolated, for example, by using PCR. In this case, the first cDNA strand may be synthesized by hybridizing an oligo-dT oligonucleotide to mRNA isolated from tissue known or suspected to be expressed in an individual putatively carrying a mutant NHP allele, and by extending the new strand with reverse transcriptase. The second strand of the cDNA is then synthesized using an oligonucleotide that hybridizes specifically to the 5' end of the normal gene. Using these two primers, the product is then amplified via PCR, optionally cloned into a suitable vector, and subjected to DNA sequence analysis through methods well known to those of skill in the art. By comparing the DNA sequence of the mutant NHP allele to that of the normal NHP allele, the mutation(s) responsible for the loss or alteration of function of the mutant NHP gene product can be ascertained.

Alternatively, a genomic library can be constructed using DNA obtained from an individual suspected of or known to carry the mutant NHP allele, or a cDNA library can be constructed using RNA from a tissue known, or suspected, to express the mutant NHP allele. A normal NHP gene, or any suitable fragment thereof, can then be labeled and used as a probe to identify the corresponding mutant NHP allele in such libraries. Clones containing the mutant NHP gene sequences may then be purified and subjected to sequence analysis according to methods well known to those of skill in the art.

Additionally, an expression library can be constructed utilizing cDNA synthesized from, for example, RNA isolated from a tissue known, or suspected, to express a mutant NHP allele in an individual suspected of or known to carry such a mutant allele. In this manner, gene products made by the putatively mutant tissue may be expressed and screened using standard antibody screening techniques in conjunction with antibodies raised against the normal NHP product, as described, below, in Section 5.3. (For screening techniques, see, for example, Harlow, E. and Lane, eds., 1988, "Antibodies: A Laboratory Manual", Cold Spring Harbor Press, Cold Spring Harbor.)

Additionally, screening can be accomplished by screening with labeled NHP fusion proteins, such as, for example, AP-NHP or NHP-AP fusion proteins. In cases where a NHP mutation results in an expressed gene product with altered function (e.g., as a result of a missense or a frameshift mutation), a polyclonal set of antibodies to NHP are likely to cross-react with the mutant NHP gene product. Library clones detected via their reaction with such labeled antibodies can be purified and subjected to sequence analysis according to methods well known to those of skill in the art.

An additional method of "screening" for NHP-related sequences (both nucleotide an amino acid) involves electronic methods of storing, retrieving, and analyzing the described sequences and derivatives thereof. Accordingly, an additional embodiment of the present invention includes computer readable electronic data storage medium, or any system incorporating the same, that comprises a representation of any contiguous stretch of sequence first disclosed in the Sequence Listing.

The invention also encompasses nucleotide sequences that encode mutant NHPs, peptide fragments of the NHPs, truncated NHPs, and NHP fusion proteins. These include, but are not limited to nucleotide sequences encoding mutant NHPs described in section 5.2 infra; polypeptides or peptides corresponding to one or more domains of the NHP or portions of these domains; truncated NHPs in which one or more of the domains is deleted, or a truncated nonfunctional NHP. Nucleotides encoding fusion proteins may include, but are not limited to, full length NHP sequences, truncated NHPs, or nucleotides encoding peptide fragments of a NHP fused to an unrelated protein or peptide, such as for example, a NHP domain fused to an Ig Fc domain which increases the stability and half life of the resulting fusion protein (e.g., NHP-Ig) in the bloodstream; or an enzyme such as a fluorescent protein or a luminescent protein which can be used as a marker.

The invention also encompasses: (a) DNA vectors that contain any of the foregoing NHP coding sequences and/or their complements (i.e., antisense); (b) DNA expression vectors that contain any of the foregoing NHP coding sequences operatively associated with a regulatory element that directs the expression of the coding sequences; (c) genetically engineered host cells that contain any of the foregoing NHP coding sequences operatively associated with a regulatory element that directs the expression of the coding sequences in the host cell; and (d) genetically engineered host cells that express an endogenous NHP gene under the control of an exogenously introduced regulatory element (i.e., gene activation). As used herein, regulatory elements include but are not limited to inducible and non-inducible promoters, enhancers, operators and other elements known to those skilled in the art that drive and regulate expression. Such regulatory elements include but are not limited to the cytomegalovirus hCMV immediate early gene, regulatable, viral (particularly retroviral LTR promoters) the early or late promoters of SV40 adenovirus, the lac system, the trp system, the TAC system, the TRC system, the major operator and promoter regions of phage lambda, the control regions of fd coat protein, the promoter for 3-phosphoglycerate kinase (PGK), the promoters of acid phosphatase, and the promoters of the yeast α-mating factors.

5.2. NHP Polypeptides

NHPs, polypeptides, peptide fragments, mutated, truncated, or deleted forms of the NHPs, and/or NHP fusion proteins can be prepared for a variety of uses, including but not limited to the generation of antibodies, as reagents in diagnostic assays, the identification of other cellular gene products related to a NHP, as reagents in assays for screening for compounds that can be as pharmaceutical reagents useful in the therapeutic treatment of mental, biological, or medical disorders and disease.

The Sequence Listing discloses the amino acid sequences encoded by the described NHP genes. The NHPs have initiator methionines in DNA sequence contexts consistent with translation initiation sites. The sequence data presented herein indicate that alternative forms (e.g., variants arising from alternative splicing, promoters, etc.) of the NHPs may exist (which may or may not be tissue specific).

The NHP amino acid sequences of the invention include the amino acid sequences presented in the Sequence Listing as well as analogues and derivatives thereof. Further, corresponding NHP homologues from other species are encompassed by the invention. In fact, any NHP protein encoded by the NHP nucleotide sequences described in Section 5.1, above, are within the scope of the invention, as are any novel polynucleotide sequences encoding all or any novel portion of an amino acid sequence presented in the Sequence Listing. The degenerate nature of the genetic code is well known, and, accordingly, each amino acid presented in the Sequence Listing, is generically representative of the well known nucleic acid "triplet" codon, or in many cases codons, that can encode the amino acid. As such, as contemplated herein, the amino acid sequences presented in the Sequence Listing, when taken together with the genetic code (see, for example, Table 4-1 at page 109 of "Molecular Cell Biology", 1986, J. Darnell et al. eds., Scientific American Books, New York, N.Y., herein incorporated by reference) are generically representative of all the various permutations and combinations of nucleic acid sequences that can encode such amino acid sequences.

The invention also encompasses proteins that are functionally equivalent to the NHPs encoded by the nucleotide sequences described in Section 5.1, as judged by any of a number of criteria, including, but not limited to, the ability to mediate lipoxygenase activity, the ability to effect an identical or complementary leukotriene pathway, a change in cellular metabolism (e.g., ion flux, tyrosine phosphorylation, etc.), or change in phenotype when the NHP equivalent is similarly expressed or mutated in an appropriate cell type (such as the amelioration, prevention or delay of a biochemical, biophysical, or overt phenotype. Such functionally equivalent NHP proteins include, but are not limited to, additions or substitutions of amino acid residues within the amino acid sequence encoded by the NHP nucleotide sequences described above, in Section 5.1, but which result in a silent change, thus producing a functionally equivalent gene product. Amino acid substitutions can be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

While random mutations can be made to NHP DNA (using random mutagenesis techniques well known to those skilled in the art) and the resulting mutant NHPs tested for activity, site-directed mutations of the NHP coding sequence can be engineered (using site-directed mutagenesis techniques well known to those skilled in the art) to generate mutant NHPs with increased function, e.g., higher lipoxygenase activity, decreased function, and/or increased physiological half-life. One starting point for such analysis is to align the disclosed human sequences with corresponding gene/protein sequences from, for example, other mammals in order to identify amino acid sequence motifs that are conserved between different species. Non-conservative changes can be engineered at variable positions to alter function, signal transduction capability, or both. Alternatively, where alteration of function is desired, deletion or non-conservative alterations of the conserved regions (i.e., identical amino acids) can be engineered.

Other mutations to the NHP coding sequence can be made to generate NHPs that are better suited for expression, scale up, etc. in the host cells chosen. For example, cysteine residues can be deleted or substituted with another amino acid in order to eliminate disulfide bridges; N-linked glycosylation sites can be altered or eliminated to achieve, for example, expression of a homogeneous product that is more easily recovered and purified from yeast hosts which are known to hyperglycosylate-linked sites. To this end, a variety of amino acid substitutions at one or both of the first or third amino acid positions of any one or more of the glycosylation recognition sequences (N-X-S or N-X-T), and/or an amino acid deletion at the second position of any one or more such recognition sequences will prevent glycosylation of the NHP at the modified tripeptide sequence. (See, e.g., Miyajima et al., 1986, EMBO J. 5(6):1193–1197).

Peptides corresponding to one or more domains of a NHP, truncated or deleted NHPs, as well as fusion proteins in which a full length NHP, a NHP peptide, or truncated NHP is fused to an unrelated protein, are also within the scope of the invention and can be designed on the basis of the presently disclosed NHP nucleotide and NHP amino acid sequences. Such fusion proteins include, but are not limited to, IgFc fusions which stabilize the NHP protein or peptide and prolong half-life in vivo; or fusions to any amino acid sequence that allows the fusion protein to be anchored to the cell membrane; or fusions to an enzyme, fluorescent protein, or luminescent protein which provide a marker function.

While the NHPs and peptides can be chemically synthesized (e.g., see Creighton, 1983, Proteins: Structures and Molecular Principles, W.H. Freeman & Co., N.Y.), large polypeptides derived from a NHP and full length NHPs can be advantageously produced by recombinant DNA technology using techniques well known in the art for expressing nucleic acid containing NHP gene sequences and/or coding sequences. Such methods can be used to construct expression vectors containing a NHP nucleotide sequences described in Section 5.1 and appropriate transcriptional and translational control signals. These methods include, for example, in vitro recombinant DNA techniques, synthetic techniques, and in vivo genetic recombination. See, for example, the techniques described in Sambrook et al., 1989, supra, and Ausubel et al., 1989, supra. For example, recombinant lipoxygenase has been successfully produced in insect cells (using baculo virus) and purified using nickel affinity chromatography. Alternatively, RNA corresponding to all or a portion of a transcript encoded by a NHP nucleotide sequence may be chemically synthesized using, for example, synthesizers. See, for example, the techniques described in "Oligonucleotide Synthesis", 1984, Gait, M. J. ed., IRL Press, Oxford, which is incorporated by reference herein in its entirety.

A variety of host-expression vector systems may be utilized to express the NHP nucleotide sequences of the invention. Where the NHP peptide or polypeptide is a soluble derivative, the peptide or polypeptide can be recovered from the culture, or from the host cell in cases where the NHP peptide or polypeptide is not secreted, and from the culture media in cases where the NHP peptide or polypeptide has been engineered to be secreted by the cells. However, such expression systems also encompass engineered host cells that express a NHP, or functional equivalent, in situ, i.e., anchored in the cell membrane. One study has indicated that the majority of one type of 15S-lipoxygenase protein can typically be found in soluble cytoplasmic cell fractions, but the majority of lipoxygenase activity can be found in the membrane fraction.

Purification or enrichment of NHP from such expression systems can be accomplished using appropriate detergents and lipid micelles and methods well known to those skilled in the art. However, such engineered host cells themselves may be used in situations where it is important to not only to retain the structural and functional characteristics of the NHP, but to assess biological activity, e.g., in drug screening assays.

The expression systems that may be used for purposes of the invention include but are not limited to microorganisms such as bacteria (e.g., *E. coli, B. subtilis*) transformed with recombinant bacteriophage DNA, plasmid DNA or cosmid DNA expression vectors containing NHP nucleotide sequences; yeast (e.g., Saccharomyces, Pichia) transformed with recombinant yeast expression vectors containing NHP nucleotide sequences; insect cell systems infected with recombinant virus expression vectors (e.g., baculo virus) containing NHP sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing NHP nucleotide sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the NHP product being expressed. For example, when a large quantity of such a protein is to be produced for the identification of molecules that inhibit or enhance NHP activity, for the generation of pharmaceutical compositions comprising NHP, or for raising antibodies to a NHP, vectors that direct the expression of high levels of fusion protein products that are readily purified may be desirable. Such vectors include, but are not limited to the *E. coli* expression vector pUR278 (Ruther et al., 1983, EMBO J. 2:1791), in which a NHP coding sequence may be ligated individually into the vector in-frame with the lacZ coding region so that a fusion protein is produced; pIN vectors (Inouye & Inouye, 1985, Nucleic Acids Res. 13:3101–3109; Van Heeke & Schuster, 1989, J. Biol. Chem. 264:5503–5509); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The PGEX vectors are designed to include thrombin or factor Xa protease cleavage sites so that the cloned target gene product can be released from the GST moiety.

In an insect system, Autographa californica nuclear polyhidrosis virus (AcNPV) is used as a vector to express foreign genes. The virus grows in *Spodoptera frugiperda* cells. A NHP gene coding sequence may be cloned individually into non-essential regions (for example the polyhedrin gene) of the virus and placed under control of an AcNPV promoter (for example the polyhedrin promoter). Successful insertion of NHP gene coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed (e.g., see Smith et al., 1983, J. Virol. 46: 584; Smith, U.S. Pat. No. 4,215,051).

In mammalian host cells, a number of viral-based expression systems may be utilized. In cases where an adenovirus is used as an expression vector, the NHP nucleotide sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing a NHP product in infected hosts (e.g., See Logan & Shenk, 1984, Proc. Natl. Acad. Sci. USA 81:3655–3659). Specific initiation signals may also be required for efficient translation of inserted NHP nucleotide sequences. These signals include the ATG initiation codon and adjacent sequences. In cases where an entire NHP gene or cDNA, including its own initiation codon and adjacent sequences, is inserted into the appropriate expression vector, no additional translational control signals may be needed. However, in cases where only a portion of a NHP coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (See Bittner et al., 1987, Methods in Enzymol. 153:516–544).

In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include, but are not limited to, CHO, VERO, BHK, HeLa, COS, MDCK, 293, 3T3, WI38, and in particular, human cell lines.

For long-term, high-yield production of recombinant proteins, stable expression is preferred. For example, cell lines which stably express the NHP sequences described above may be engineered. Rather than using expression vectors that contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines that express a NHP product. Such engineered cell lines may be particularly useful in screening and evaluation of compounds that affect the endogenous activity of the NHP product.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in tk$^-$, hgprt or aprt cells, respectively. Also, antimetabolite resistance can be used as the basis of selection for the following genes: dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147).

Alternatively, any fusion protein may be readily purified by utilizing an antibody specific for the fusion protein being expressed. For example, a system described by Janknecht et al. allows for the ready purification of non-denatured fusion proteins expressed in human cell lines (Janknecht, et al., 1991, Proc. Natl. Acad. Sci. USA 88: 8972–8976). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$-nitriloacetic acid-agarose columns and histidine-tagged proteins are selectively eluted with imidazole-containing buffers.

NHP products can also be expressed in transgenic animals. Animals of any species, including, but not limited to, worms, mice, rats, rabbits, guinea pigs, pigs, micro-pigs, birds, goats, and non-human primates, e.g., baboons, monkeys, and chimpanzees may be used to generate NHP transgenic animals.

Any technique known in the art may be used to introduce a NHP transgene into animals to produce the founder lines of transgenic animals. Such techniques include, but are not limited to pronuclear microinjection (Hoppe, P. C. and Wagner, T. E., 1989, U.S. Pat. No. 4,873,191); retrovirus mediated gene transfer into germ lines (Van der Putten et al., 1985, Proc. Natl. Acad. Sci., USA 82:6148–6152); gene targeting in embryonic stem cells (Thompson et al., 1989, Cell 56:313–321); electroporation of embryos (Lo, 1983, Mol Cell. Biol. 3:1803–1814); and sperm-mediated gene transfer (Lavitrano et al., 1989, Cell 57:717–723); etc. For a review of such techniques, see Gordon, 1989, Transgenic Animals, Intl. Rev. Cytol. 115:171–229, which is incorporated by reference herein in its entirety.

The present invention provides for transgenic animals that carry the NHP transgene in all their cells, as well as animals which carry the transgene in some, but not all their cells, i.e., mosaic animals or somatic cell transgenic animals. The transgene may be integrated as a single transgene or in concatamers, e.g., head-to-head tandems or head-to-tail tandems. The transgene may also be selectively introduced into and activated in a particular cell type by following, for example, the teaching of Lasko et al., 1992, Proc. Natl. Acad. Sci. USA 89:6232–6236. The regulatory sequences required for such a cell-type specific activation will depend upon the particular cell type of interest, and will be apparent to those of skill in the art.

When it is desired that the NHP gene transgene be integrated into the chromosomal site of the endogenous NHP gene, gene targeting is preferred. Briefly, when such a technique is to be utilized, vectors containing some nucleotide sequences homologous to the endogenous NHP gene are designed for the purpose of integrating, via homologous recombination with chromosomal sequences, into and disrupting the function of the nucleotide sequence of the endogenous NHP gene (i.e., "knockout" animals).

The transgene may also be selectively introduced into a particular cell type, thus inactivating the endogenous NHP gene in only that cell type, by following, for example, the teaching of Gu et al., 1994, Science, 265:103–106. The regulatory sequences required for such a cell-type specific inactivation will depend upon the particular cell type of interest, and will be apparent to those of skill in the art.

Once transgenic animals have been generated, the expression of the recombinant NHP gene may be assayed utilizing standard techniques. Initial screening may be accomplished by Southern blot analysis or PCR techniques to analyze animal tissues to assay whether integration of the transgene has taken place. The level of mRNA expression of the transgene in the tissues of the transgenic animals may also be assessed using techniques which include but are not limited to Northern blot analysis of tissue samples obtained from the animal, in situ hybridization analysis, and RT-PCR. Samples of NHP gene-expressing tissue, may also be evaluated immunocytochemically using antibodies specific for the NHP transgene product.

5.3. Antibodies to NHPs

Antibodies that specifically recognize one or more epitopes of a NHP, or epitopes of conserved variants of a NHP, or peptide fragments of a NHP are also encompassed by the invention. Such antibodies include but are not limited to polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above.

The antibodies of the invention may be used, for example, in the detection of NHP in a biological sample and may, therefore, be utilized as part of a diagnostic or prognostic technique whereby patients may be tested for abnormal amounts of NHP. Such antibodies may also be utilized in conjunction with, for example, compound screening schemes, as described, below, in Section 5.5, for the evaluation of the effect of test compounds on expression and/or activity of a NHP gene product. Additionally, such antibodies can be used in conjunction gene therapy to, for example, evaluate the normal and/or engineered NHP-expressing cells prior to their introduction into the patient. Such antibodies may additionally be used as a method for the inhibition of abnormal NHP activity. Thus, such antibodies, domains thereof, or peptides therefrom, may be utilized as part of treatment methods.

For the production of antibodies, various host animals may be immunized by injection with the NHP, an NHP peptide (e.g., one corresponding to a functional domain of an NHP), truncated NHP polypeptides (NHP in which one or more domains have been deleted), functional equivalents of the NHP or mutants of the NHP. Such host animals may include but are not limited to rabbits, mice, goats, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and Corynebacterium parvum. Polyclonal antibodies are heterogeneous populations of antibody molecules derived from the sera of the immunized animals.

Monoclonal antibodies, which are homogeneous populations of antibodies to a particular antigen, may be obtained by any technique which provides for the production of antibody molecules by continuous cell lines in culture. These include, but are not limited to, the hybridoma technique of Kohler and Milstein, (1975, Nature 256:495–497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 334:544–546) can be adapted to produce single chain antibodies against NHP gene products. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include, but are not limited to: the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries may be constructed (Huse et al., 1989, Science, 246:1275–1281) to allow rapid and easy identification of monoclonal Fab fragments with the desired specificity.

Antibodies to a NHP can, in turn, be utilized to generate anti-idiotype antibodies that "mimic" a given NHP, using techniques well known to those skilled in the art. (See, e.g., Greenspan & Bona, 1993, FASEB J 7(5):437–444; and Nissinoff, 1991, J. Immunol. 147(8):2429–2438). For example antibodies which bind to a NHP domain and competitively inhibit the binding of NHP to its cognate receptor can be used to generate anti-idiotypes that "mimic" the NHP and, therefore, bind and activate or neutralize a receptor. Such anti-idiotypic antibodies or Fab fragments of such anti-idiotypes can be used in therapeutic regimens involving the NHP signaling pathway.

5.4. Diagnosis of Abnormalities Related to a NHP

A variety of methods can be employed for the diagnostic and prognostic evaluation of disorders related to NHP function, and for the identification of subjects having a predisposition to such disorders.

Such methods may, for example, utilize reagents such as the NHP nucleotide sequences described in Section 5.1, and NHP antibodies, as described, in Section 5.3. Specifically, such reagents may be used, for example, for: (1) the detection of the presence of NHP gene mutations, or the detection of either over- or under-expression of NHP mRNA relative to a given phenotype; (2) the detection of either an over- or an under-abundance of NHP gene product relative to a given phenotype; and (3) the detection of perturbations or abnormalities in any potential signal transduction, metabolic, or catabolic pathway mediated by a NHP.

The methods described herein may be performed, for example, by utilizing pre-packaged diagnostic kits comprising at least one specific NHP nucleotide sequence or NHP antibody reagent described herein, which may be conveniently used, e.g., in clinical settings, to diagnose patients exhibiting inflammatory disorders.

For the detection of NHP mutations, any nucleated cell can be used as a starting source for genomic nucleic acid. For the detection of NHP gene expression or NHP gene products, any cell type or tissue in which the NHP gene is expressed, such as, for example, skin, testis, or brain cells, may be utilized.

Nucleic acid-based detection techniques are described, below, in Section 5.4.1. Peptide detection techniques are described, below, in Section 5.4.2.

5.4.1. Detection of NHP Polynucleotides

Mutations within a NHP gene can be detected by utilizing a number of techniques. Nucleic acid from any nucleated cell can be used as the starting point for such assay techniques, and may be isolated according to standard nucleic acid preparation procedures which are well known to those of skill in the art.

DNA may be used in hybridization or amplification assays of biological samples to detect abnormalities involving NHP gene structure, including point mutations, insertions, deletions and chromosomal rearrangements. Such assays may include, but are not limited to, Southern analyses, single stranded conformational polymorphism analyses (SSCP), and PCR analyses.

Such diagnostic methods for the detection of NHP gene-specific mutations can involve for example, contacting and incubating nucleic acids including recombinant DNA molecules, cloned genes or degenerate variants thereof, obtained from a sample, e.g., derived from a patient sample or other appropriate cellular source, with one or more labeled nucleic acid reagents including recombinant DNA molecules, cloned genes or degenerate variants thereof, as described in Section 5.1, under conditions favorable for the specific annealing of these reagents to their complementary sequences within a given NHP gene. Preferably, the lengths of these nucleic acid reagents are at least 15 to 30 nucleotides. After incubation, all non-annealed nucleic acids are removed from the nucleic acid:NHP molecule hybrid. The presence of nucleic acids which have hybridized, if any such molecules exist, is then detected. Using such a detection scheme, the nucleic acid from the cell type or tissue of interest can be immobilized, for example, to a solid support such as a membrane, or a plastic surface such as that on a microtiter plate or polystyrene beads. In this case, after incubation, non-annealed, labeled nucleic acid reagents of the type described in Section 5.1 are easily removed. Detection of the remaining, annealed, labeled NHP nucleic acid reagents is accomplished using standard techniques well-known to those in the art. The NHP gene sequences to which the nucleic acid reagents have annealed can be compared to the annealing pattern expected from a normal NHP gene sequence in order to determine whether a NHP gene mutation is present.

Alternative diagnostic methods for the detection of NHP gene specific nucleic acid molecules, in patient samples or other appropriate cell sources, may involve their amplification, e.g., by PCR (the experimental embodiment set forth in Mullis, K. B., 1987, U.S. Pat. No. 4,683,202), followed by the detection of the amplified molecules using techniques well known to those of skill in the art. The resulting amplified sequences can be compared to those which would be expected if the nucleic acid being amplified contained only normal copies of a NHP gene in order to determine whether a NHP gene mutation exists.

Additionally, well-known genotyping techniques can be performed to identify individuals carrying NHP gene mutations. Such techniques include, for example, the use of restriction fragment length polymorphisms (RFLPs), which involve sequence variations in one of the recognition sites for the specific restriction enzyme used.

Additionally, improved methods for analyzing DNA polymorphisms which can be utilized for the identification of NHP gene mutations have been described which capitalize on the presence of variable numbers of short, tandemly repeated DNA sequences between the restriction enzyme sites. For example, Weber (U.S. Pat. No. 5,075,217, which is incorporated herein by reference in its entirety) describes a DNA marker based on length polymorphisms in blocks of (dC-dA)n-(dG-dT)n short tandem repeats. The average separation of (dC-dA)n-(dG-dT)n blocks is estimated to be 30,000–60,000 bp. Markers which are so closely spaced exhibit a high frequency co-inheritance, and are extremely useful in the identification of genetic mutations, such as, for example, mutations within a given NHP gene, and the diagnosis of diseases and disorders related to NHP mutations.

Also, Caskey et al. (U.S. Pat. No. 5,364,759, which is incorporated herein by reference in its entirety) describe a DNA profiling assay for detecting short tri and tetra nucleotide repeat sequences. The process includes extracting the DNA of interest, such as the NHP gene, amplifying the extracted DNA, and labeling the repeat sequences to form a genotypic map of the individual's DNA.

An additional embodiment of the present invention involves identifying the association between NHPs, or NHP variants, and disease. Using such associations, individuals can be identified that harbor NHP variants or display NHP expression profiles that correlate with a given disease (e.g., dermatoses, asthma, IBD, etc.). Once such a genetic diagnosis has been established using single nucleotide polymorphisms (SNPs), coding SNPs (cSNPs), etc., an appropriate treatment regimen can be tailored to the patient.

The level of NHP gene expression can also be assayed by detecting and measuring NHP transcription. For example, RNA from a cell type or tissue known, or suspected to express the NHP gene, such as skin, testis, or brain, may be isolated and tested utilizing hybridization or PCR techniques such as are described, above. The isolated cells can be derived from cell culture or from a patient. The analysis of cells taken from culture may be a necessary step in the assessment of cells to be used as part of a cell-based gene therapy technique or, alternatively, to test the effect of compounds on the expression of the NHP gene. Such analyses may reveal both quantitative and qualitative aspects of the expression pattern of the NHP gene, including activation or inactivation of NHP gene expression. A preferred method of conducting such screening assays uses the described sequences as part of a larger array of sequences (i.e., microchip arrays, etc.).

In one embodiment of such a detection scheme, cDNAs are synthesized from the RNAs of interest (e.g., by reverse transcription of the RNA molecule into cDNA). A sequence within the cDNA is then used as the template for a nucleic acid amplification reaction, such as a PCR amplification reaction, or the like. The nucleic acid reagents used as synthesis initiation reagents (e.g., primers) in the reverse transcription and nucleic acid amplification steps of this method are chosen from among the NHP nucleic acid reagents described in Section 5.1. The preferred lengths of such nucleic acid reagents are at least 9–30 nucleotides. For detection of the amplified product, the nucleic acid amplification may be performed using radioactively or non-radioactively labeled nucleotides. Alternatively, enough amplified product may be made such that the product may be visualized by standard ethidium bromide staining, by utilizing any other suitable nucleic acid staining method, or by sequencing.

Additionally, it is possible to perform such NHP gene expression assays "in situ", i.e., directly upon tissue sections (fixed and/or frozen) of patient tissue obtained from biopsies or resections, such that no nucleic acid purification is necessary. Nucleic acid reagents such as those described in Section 5.1 may be used as probes and/or primers for such in situ procedures (See, for example, Nuovo, G. J., 1992, "PCR In Situ Hybridization: Protocols And Applications", Raven Press, NY).

Alternatively, if a sufficient quantity of the appropriate cells can be obtained, standard Northern analysis can be performed to determine the level of mRNA expression of the NHP gene.

5.4.2. Detection of NHP Polypeptides

Antibodies directed against wild type or mutant NHP products or conserved variants or peptide fragments thereof, which are discussed, above, in Section 5.3, may also be used as diagnostics and prognostics, as described herein. Such diagnostic methods, may be used to detect abnormalities in the level of NHP gene expression, or abnormalities in the structure and/or temporal, tissue, cellular, or subcellular location of the NHP, and may be performed in vivo or in vitro, such as, for example, on biopsy tissue.

For example, antibodies directed to epitopes of an NHP can be used in vivo to detect the pattern and level of expression of the NHP in the body. Such antibodies can be labeled, e.g., with a radio-opaque or other appropriate compound and injected into a subject in order to visualize binding to the NHP expressed in the body using methods such as X-rays, CAT-scans, or MRI. Labeled antibody fragments, e.g., the Fab or single chain antibody comprising the smallest portion of the antigen binding region, are preferred for this purpose to promote crossing the blood-brain barrier and permit labeling of NHPs expressed in the brain.

Additionally, any NHP fusion protein or NHP conjugated protein whose presence can be detected, can be administered. For example, NHP fusion or conjugated proteins labeled with a radio-opaque or other appropriate compound can be administered and visualized in vivo, as discussed, above for labeled antibodies. Further such NHP fusion proteins (such as AP-NHP or NHP-AP) can be utilized for in vitro diagnostic procedures.

Alternatively, immunoassays or fusion protein detection assays, as described above, can be utilized on biopsy and autopsy samples in vitro to permit assessment of the expression pattern of the NHP. Such assays are not confined to the use of antibodies that define a NHP domain, but can include the use of antibodies directed to epitopes of any domain of a NHP. The use of each or all of these labeled antibodies will yield useful information regarding translation and intracellular transport of the NHP to the cell surface and can identify defects in processing.

The tissue or cell type to be analyzed will generally include those which are known, or suspected, to express the NHP gene, such as, for example, epithelial cells, brain cells, etc. The protein isolation methods employed herein may, for example, be such as those described in Harlow and Lane (Harlow, E. and Lane, D., 1988, "Antibodies: A Laboratory Manual", Cold Spring Harbor Laboratory Press, Cold Spring Harbor, N.Y.), which is incorporated herein by reference in its entirety. The isolated cells can be derived from cell culture or from a patient. The analysis of cells taken from culture may be a necessary step in the assessment of cells that could be used as part of a cell-based gene therapy technique or, alternatively, to test the effect of compounds on the expression of a NHP gene.

For example, antibodies, or fragments of antibodies, such as those described, above, in Section 5.3, useful in the present invention may be used to quantitatively or qualitatively detect the presence of NHP products or conserved variants or peptide fragments thereof. This can be accomplished, for example, by immunofluorescence techniques employing a fluorescently labeled antibody (see below, this Section) coupled with light microscopic, flow cytometric, or fluorimetric detection. Such techniques are especially preferred if such NHP products are at least transiently present on the cell surface.

The antibodies (or fragments thereof) or NHP fusion or conjugated proteins useful in the present invention may, additionally, be employed histologically, as in immunofluorescence, immunoelectron microscopy or non-immuno assays, for in situ detection of NHP gene products or conserved variants or peptide fragments thereof, or to assay NHP binding (in the case of labeled NHP-fusion protein).

In situ detection may be accomplished by removing a histological specimen from a patient, and applying thereto a labeled antibody or fusion protein of the present invention. The antibody (or fragment) or fusion protein is preferably applied by overlaying the labeled antibody (or fragment) onto a biological sample. Through the use of such a procedure, it is possible to determine not only the presence of the NHP product, or conserved variants or peptide fragments, or NHP binding, but also its distribution in the examined tissue. Using the present invention, those of ordinary skill will readily perceive that any of a wide variety of histological methods (such as staining procedures) can be modified in order to achieve such in situ detection.

Immunoassays and non-immunoassays for NHP products, or conserved variants or peptide fragments thereof, will typically comprise incubating a sample, such as a biological fluid, a tissue extract, freshly harvested cells, or lysates of cells which have been incubated in cell culture, in the presence of a detectably labeled antibody capable of identifying NHP products or conserved variants or peptide fragments thereof, and detecting the bound antibody by any of a number of techniques well-known in the art. Alternatively, the labeled antibody can be directed against an antigenic tag that has been directly or indirectly attached to a NHP.

The biological sample may be brought in contact with and immobilized onto a solid phase support or carrier such as nitrocellulose, or other solid support which is capable of immobilizing cells, cell particles or soluble proteins. The support may then be washed with suitable buffers followed by treatment with the detectably labeled NHP antibody or NHP receptor fusion protein. The solid phase support may then be washed with the buffer a second time to remove unbound antibody or fusion protein. The amount of bound label on solid support may then be detected by conventional means.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

The binding activity of a given lot of NHP antibody or NHP ligand fusion protein may be determined according to well known methods. Those skilled in the art will be able to determine operative and optimal assay conditions for each determination by employing routine experimentation.

With respect to antibodies, one of the ways in which the NHP antibody can be detectably labeled is by linking the same to an enzyme and use in an enzyme immunoassay (EIA) (Voller, A., "The Enzyme Linked Immunosorbent Assay (ELISA)", 1978, Diagnostic Horizons 2:1–7, Microbiological Associates Quarterly Publication, Walkersville, Md.); Voller, A. et al., 1978, J. Clin. Pathol. 31:507–520; Butler, J. E., 1981, Meth. Enzymol. 73:482–523; Maggio, E. (ed.), 1980, Enzyme Immunoassay, CRC Press, Boca Raton, Fla.; Ishikawa, E. et al., (eds.), 1981, Enzyme Immunoassay, Kgaku Shoin, Tokyo). The enzyme that is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect NHP through the use of a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

5.5. Screening Assays for Compounds that Modulate NHP Expression or Activity

The following assays are designed to identify compounds that interact with (e.g., bind to) NHPs, compounds that interfere NHP activity, compounds that modulate the activity of NHP gene expression (i.e., modulate the level of NHP gene expression) or compounds that modulate the levels of NHP in the body. Assays may additionally be utilized that identify compounds that bind to NHP gene regulatory sequences (e.g., promoter sequences) and, consequently, can modulate NHP gene expression. See e.g., Platt, K. A., 1994, J. Biol. Chem. 269:28558–28562, which is incorporated herein by reference in its entirety.

The compounds that can be screened in accordance with the invention include but are not limited to peptides, antibodies and fragments thereof, and other organic compounds (e.g., peptidomimetics) that bind to a NHP and inhibit, hinder, or enhance lipoxygenase activity.

Such compounds may include, but are not limited to, peptides such as, for example, soluble peptides, including but not limited to members of random peptide libraries; (see, e.g., Lam, K. S. et al., 1991, Nature 354:82–84; Houghten, R. et al., 1991, Nature 354:84–86), and combinatorial chemistry-derived molecular libraries made of D- and/or L-configuration amino acids, phosphopeptides (including, but not limited to members of random or partially degenerate, directed phosphopeptide libraries; see, e.g., Songyang, Z. et al., 1993, Cell 72:767–778), antibodies (including, but not limited to, polyclonal, monoclonal, humanized, anti-idiotypic, chimeric or single chain antibodies, and FAb, F(ab')$_2$ and FAb expression library fragments, and epitope-binding fragments thereof), and small organic or inorganic molecules.

Other compounds which can be screened in accordance with the invention include but are not limited to small organic molecules that are able to cross the blood-brain barrier, gain entry into an appropriate cell (e.g., in the choroid plexus, pituitary, the hypothalamus, etc.) and affect the expression of a NHP gene or some other gene involved in a NHP mediated pathway (e.g., by interacting with the regulatory region or transcription factors involved in gene expression or translation); or such compounds that affect NHP-mediated leukotriene synthesis, or catabolic, inflammatory, or metabolic pathways.

Computer modeling and searching technologies permit identification of compounds, or the improvement of already identified compounds, that can modulate NHP expression or activity. Having identified such a compound or composition, the active sites or regions are identified. Such active sites might typically be ligand or substrate binding sites. The active site can be identified using methods known in the art including, for example, from the amino acid sequences of peptides, from the nucleotide sequences of nucleic acids, or from study of complexes of the relevant compound or composition with its natural ligand. In the latter case, chemical or X-ray crystallographic methods can be used to find the active site by finding where on the factor the complexed ligand is found.

Next, the three dimensional geometric structure of the active site is determined. This can be done by known methods, including X-ray crystallography, which can determine a complete molecular structure. On the other hand, solid or liquid phase NMR can be used to determine certain intra-molecular distances. Any other experimental method of structure determination can be used to obtain partial or complete geometric structures. The geometric structures may be measured with a complexed ligand, natural or artificial, which may increase the accuracy of the active site structure determined.

If an incomplete or insufficiently accurate structure is determined, the methods of computer based numerical modeling can be used to complete the structure or improve its accuracy. Any recognized modeling method may be used, including parameterized models specific to particular biopolymers such as proteins or nucleic acids, molecular dynamics models based on computing molecular motions, statistical mechanics models based on thermal ensembles, or combined models. For most types of models, standard molecular force fields, representing the forces between constituent atoms and groups, are necessary, and can be selected from force fields known in physical chemistry. The incomplete or less accurate experimental structures can serve as constraints on the complete and more accurate structures computed by these modeling methods.

Finally, having determined the structure of the active site (or binding site), either experimentally, by modeling, or by a combination, candidate modulating compounds can be identified by searching databases containing compounds along with information on their molecular structure. Such a search seeks compounds having structures that match the determined active site structure and that interact with the groups defining the active site. Such a search can be manual, but is preferably computer assisted. These compounds found from this search are potential NHP modulating compounds.

Alternatively, these methods can be used to identify improved modulating compounds from an already known modulating compound or ligand. The composition of the known compound can be modified and the structural effects of modification can be determined using the experimental and computer modeling methods described above applied to the new composition. The altered structure is then compared to the active site structure of the compound to determine if an improved fit or interaction results. In this manner systematic variations in composition, such as by varying side groups, can be quickly evaluated to obtain modified modulating compounds or ligands of improved specificity or activity.

Further experimental and computer modeling methods useful to identify modulating compounds based upon identification of the active sites (or binding sites) of a NHP, and related transduction and transcription factors will be apparent to those of skill in the art.

Examples of molecular modeling systems are the CHARMm and QUANTA programs (Polygen Corporation, Waltham, Mass.). CHARMm performs the energy minimization and molecular dynamics functions. QUANTA performs the construction, graphic modeling and analysis of molecular structure. QUANTA allows interactive construction, modification, visualization, and analysis of the behavior of molecules with each other.

A number of articles review computer modeling of drugs interactive with specific proteins, such as Rotivinen, et al., 1988, Acta Pharmaceutical Fennica 97:159–166; Ripka, New Scientist 54–57 (Jun. 16, 1988); McKinaly and Rossmann, 1989, Annu. Rev. Pharmacol. Toxiciol. 29:111–122; Perry and Davies, OSAR: Quantitative Structure-Activity Relationships in Drug Design pp. 189–193 (Alan R. Liss, Inc. 1989); Lewis and Dean, 1989 Proc. R. Soc. Lond. 236:125–140 and 141–162; and, with respect to a model receptor for nucleic acid components, Askew, et al., 1989, J. Am. Chem. Soc. 111:1082–1090. Other computer programs that screen and graphically depict chemicals are available from companies such as BioDesign, Inc. (Pasadena, Calif.), Allelix, Inc. (Mississauga, Ontario, Canada), and Hypercube, Inc. (Cambridge, Ontario). Although these are primarily designed for application to drugs specific to particular proteins, they can be adapted to design of drugs specific to regions of DNA or RNA, once that region is identified.

Although described above with reference to design and generation of compounds which could alter binding, one could also screen libraries of known compounds, including natural products or synthetic chemicals, and biologically active materials, including proteins, for compounds which are inhibitors or activators.

Cell-based systems can also be used to identify compounds that bind (or mimic) NHPs as well as assess the altered activity associated with such binding in living cells. One tool of particular interest for such assays is green fluorescent protein which is described, inter alia, in U.S. Pat. No. 5,625,048, herein incorporated by reference. Cells that may be used in such cellular assays include, but are not limited to, leukocytes, or cell lines derived from leukocytes, lymphocytes, stem cells, including embryonic stem cells, and the like. In addition, expression host cells (e.g., B95 cells, COS cells, CHO cells, OMK cells, fibroblasts, Sf9 cells) genetically engineered to express a functional NHP of interest and to respond to activation by the test, or natural, ligand, as measured by a chemical or phenotypic change, or induction of another host cell gene, can be used as an end point in the assay.

Compounds identified via assays such as those described herein may be useful, for example, in elucidating the biological function of a NHP product. Such compounds can be administered to a patient at therapeutically effective doses to treat any of a variety of physiological or mental disorders. A therapeutically effective dose refers to that amount of the compound sufficient to result in any amelioration, impediment, prevention, or alteration of any biological symptom.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Pharmaceutical compositions for use in accordance with the present invention may be formulated in conventional manner using one or more physiologically acceptable carriers or excipients. Thus, the compounds and their physiologically acceptable salts and solvates may be formulated for administration by inhalation or insufflation (either through the mouth or the nose) or oral, buccal, parenteral, intracranial, intrathecal, topical (skin creams, ointments, etc.), or rectal administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insulator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

5.5.1. In Vitro Screening Assays for Compounds that Bind to NHPs

In vitro systems may be designed to identify compounds capable of interacting with (e.g., binding to) NHPs. The compounds identified can be useful, for example, in modulating the activity of wild type and/or mutant NHP products; can be useful in elaborating the biological function of the NHP; can be utilized in screens for identifying compounds that disrupt normal NHP interactions; or may themselves disrupt or activate such interactions.

The principle of the assays used to identify compounds that bind to NHPs, involves preparing a reaction mixture of an NHP and the test compound under conditions and for a time sufficient to allow the two components to interact and bind, thus forming a complex which can be removed and/or detected in the reaction mixture. The NHP species used can vary depending upon the goal of the screening assay. For example, where compounds that directly interact with the NHP are sought, full-length NHP, peptides corresponding to the NHP, or fusion proteins containing NHPs can be used.

The screening assays can be conducted in a variety of ways. For example, one method to conduct such an assay would involve anchoring the NHP, polypeptide, peptide, or fusion protein therefrom, or the test substance onto a solid phase and detecting NHP/test compound complexes anchored on the solid phase at the end of the reaction. In one embodiment of such a method, the NHP reactant may be anchored onto a solid surface, and the test compound, which is not anchored, may be labeled, either directly or indirectly.

In practice, microtiter plates may conveniently be utilized as the solid phase. The anchored component may be immobilized by non-covalent or covalent attachments. Non-covalent attachment may be accomplished by simply coating the solid surface with a solution of the protein and drying. Alternatively, an immobilized antibody, preferably a monoclonal antibody, specific for the protein to be immobilized may be used to anchor the protein to the solid surface. The surfaces may be prepared in advance and stored.

In order to conduct the assay, the nonimmobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously nonimmobilized component is pre-labeled, the detection of label immobilized on the surface indicates that complexes were formed. Where the previously nonimmobilized component is not pre-labeled, an indirect label can be used to detect complexes anchored on the surface; e.g., using a labeled antibody specific for the previously nonimmobilized component (the antibody, in turn, may be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for a NHP protein, polypeptide, peptide or fusion protein or the test compound to anchor any complexes formed in solution, and a labeled antibody specific for the other component of the possible complex to detect anchored complexes.

Alternatively, cell-based assays can be used to identify compounds that interact with NHP. To this end, cell lines that express a NHP or cell lines (e.g., COS cells, CHO cells, fibroblasts, etc.) that have been genetically engineered to express NHP (e.g., by transfection or transduction of suitably engineered NHP DNA) can be used. Interaction of the test compound with, for example, a NHP expressed by the host cell can be determined by comparison to cells that do not express the NHP.

5.5.2. Assays for Intracellular Proteins that are Associated with NHP

Any method suitable for detecting protein-protein interactions may be employed for identifying membrane proteins or intracellular proteins that directly or indirectly interact with a NHP. For direct interactions, the traditional methods that can be employed include, but are not limited to, co-immunoprecipitation, crosslinking and co-purification through gradients or chromatographic columns of cell lysates or proteins obtained from cell lysates and a NHP to identify proteins in the lysate that interact with the NHP. For these assays, the NHP component can be a full length NHP, a soluble derivative of a NHP, a NHP peptide, or a NHP fusion protein. Once isolated, such an intracellular protein can be identified and can, in turn, be used, in conjunction with standard techniques, to identify proteins with which it interacts. For example, at least a portion of the amino acid sequence of an intracellular protein which interacts with a NHP can be ascertained using techniques known in the art, such as Edman degradation. (See, e.g., Creighton, 1983, "Proteins: Structures and Molecular Principles", W. H. Freeman & Co., N.Y., pp.34–49). The amino acid sequence obtained may be used as a guide for the generation of oligonucleotide mixtures that can be used to screen for gene sequences encoding such intracellular proteins. Screening may be accomplished, for example, by standard hybridization or PCR techniques. Techniques for the generation of oligonucleotide mixtures and the screening are well-known. (See, e.g., Ausubel, supra, and PCR Protocols: A Guide to Methods and Applications, 1990, Innis, M. et al., eds. Academic Press, Inc., New York).

Additionally, methods can be employed that result in the simultaneous identification of genes that encode transmembrane or intracellular proteins that interact with the NHP. These methods include, for example, probing expression libraries, in a manner similar to the well known technique of antibody probing of λgt11 libraries, using labeled NHP protein, or an NHP polypeptide, peptide or fusion protein, e.g., an NHP polypeptide or NHP domain fused to a marker (e.g., an enzyme, fluor, luminescent protein, or dye), or an Ig-Fc domain.

One method that detects protein interactions in vivo, the two-hybrid system, is described in detail for illustration only and not by way of limitation. One version of this system has been described (Chien et al., 1991, Proc. Natl. Acad. Sci. USA, 88:9578–9582) and is commercially available from Clontech (Palo Alto, Calif.).

Briefly, utilizing such a system, plasmids are constructed that encode two hybrid proteins: one plasmid consists of nucleotides encoding the DNA-binding domain of a transcription activator protein fused to a nucleotide sequence encoding a NHP, or NHP polypeptide, peptide, or fusion protein therefrom, and the other plasmid consists of nucleotides encoding the transcription activator protein's activation domain fused to a cDNA encoding an unknown protein which has been recombined into this plasmid as part of a cDNA library. The DNA-binding domain fusion plasmid and the cDNA library are transformed into a strain of the yeast *Saccharomyces cerevisiae* that contains a reporter gene (e.g., HBS or lacZ) whose regulatory region contains the transcription activator's binding site. Either hybrid protein alone cannot activate transcription of the reporter gene: the DNA-binding domain hybrid cannot because it does not provide activation function and the activation domain hybrid cannot because it cannot localize to the activator's binding sites. Interaction of the two hybrid proteins reconstitutes the functional activator protein and results in expression of the reporter gene, which is detected by an assay for the reporter gene product.

The two-hybrid system or related methodology may be used to screen activation domain libraries for proteins that interact with the "bait" gene product. By way of example, and not by way of limitation, a NHP can be used as the bait product. Total genomic or cDNA sequences are fused to the DNA encoding an activation domain. This library and a plasmid encoding a hybrid of a bait NHP gene product fused to the DNA-binding domain are cotransformed into a yeast reporter strain, and the resulting transformants are screened for those that express the reporter gene. For example, and not by way of limitation, a bait NHP gene sequence, such as the open reading frame of a NHP (or a domain of a NHP) can be cloned into a vector such that it is translationally fused to the DNA encoding the DNA-binding domain of the GAL4 protein. These colonies are purified and the library plasmids responsible for reporter gene expression are isolated. DNA sequencing is then used to identify the proteins encoded by the library plasmids.

A cDNA library of the cell line from which proteins that interact with bait NHP gene product are to be detected can be made using methods routinely practiced in the art. According to the particular system described herein, for example, the cDNA fragments can be inserted into a vector such that they are translationally fused to the transcriptional activation domain of GAL4. This library can be co-transformed along with the bait NHP gene-GAL4 fusion plasmid into a yeast strain which contains a lacZ gene driven by a promoter which contains GAL4 activation sequence. A cDNA encoded protein, fused to GAL4 transcriptional activation domain, that interacts with bait NHP gene product will reconstitute an active GAL4 protein and thereby drive expression of the HIS3 gene. Colonies which express HIS3 can be detected by their growth on petri dishes containing semi-solid agar based media lacking histidine. The cDNA can then be purified from these strains, and used to produce and isolate the bait NHP gene-interacting protein using techniques routinely practiced in the art.

5.5.3. Assays for Compounds that Interfere with NHP/Intracellular Macromolecule or NHP/Transmembrane Macromolecule Interaction Macromolecules that interact with NHPs are referred to, for purposes of this discussion, as "binding partners". These binding partners are likely to be involved in NHP mediated biological pathways. Therefore, it is desirable to identify compounds that interfere with or disrupt the interaction of such binding partners which may be useful in regulating or augmenting NHP activity in the body and/or controlling disorders associated with NHP activity (or a deficiency thereof).

The basic principle of the assay systems used to identify compounds that interfere with the interaction between a NHP or NHP receptor (collectively, the NHP moiety), and its binding partner or partners involves preparing a reaction mixture containing NHP, or NHP polypeptides, peptides or fusion proteins as described in Sections 5.5.1 and 5.5.2 above, and the binding partner under conditions and for a time sufficient to allow the two to interact and bind, thus forming a complex. In order to test a compound for inhibitory activity, the reaction mixture is prepared in the presence and absence of the test compound. The test compound may be initially included in the reaction mixture, or may be added at a time subsequent to the addition of the NHP moiety and its binding partner. Control reaction mixtures are incubated without the test compound or with a placebo. The formation of any complexes between the NHP moiety and the binding partner is then detected. The formation of a complex in the control reaction, but not in the reaction mixture containing the test compound, indicates that the compound interferes with the interaction of the NHP moiety and the interactive binding partner. Additionally, complex formation within reaction mixtures containing the test compound and normal NHP protein may also be compared to complex formation within reaction mixtures containing the test compound and a mutant NHP. This comparison may be important in those cases wherein it is desirable to identify compounds that specifically disrupt interactions of mutant, or mutated, NHPs but not normal NHPs, or other lipoxygenases.

The assay for compounds that interfere with the interaction of the NHP and binding partners can be conducted in a heterogeneous or homogenous format. Heterogeneous assays involve anchoring either the NHP moiety or the binding partner onto a solid phase and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction by competition can be identified by conducting the reaction in the presence of the test substance; i.e., by adding the test substance to the reaction mixture prior to, or simultaneously with, a NHP moiety and interactive binding partner. Alternatively, test compounds that disrupt preformed complexes, e.g. compounds with higher binding constants that displace one of the components from the complex, can be tested by adding the test compound to the reaction mixture after complexes have been formed. The various formats are described briefly below.

In a heterogeneous assay system, either a NHP moiety or an interactive binding partner, is anchored onto a solid surface, while the non-anchored species is labeled, either directly or indirectly. In practice, microtiter plates are conveniently utilized. The anchored species may be immobilized by non-covalent or covalent attachments. Non-covalent attachment may be accomplished simply by coating the solid surface with a solution of the NHP moiety or binding partner and drying. Alternatively, an immobilized antibody specific for the species to be anchored may be used to anchor the species to the solid surface. The surfaces may be prepared in advance and stored.

In order to conduct the assay, the partner of the immobilized species is exposed to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, may be directly labeled or indirectly labeled with a labeled anti-Ig antibody). Depending upon the order of addition of reaction components, test compounds which inhibit complex formation or which disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds which inhibit complex or which disrupt preformed complexes can be identified.

In an alternate embodiment of the invention, a homogeneous assay can be used. In this approach, a preformed complex of a NHP moiety and an interactive binding partner is prepared in which either the NHP moiety or its binding partners is labeled, but the signal generated by the label is quenched due to formation of the complex (see, e.g., U.S. Pat. No. 4,109,496 by Rubenstein which utilizes this approach for immunoassays). The addition of a test substance that competes with and displaces one of the species from the preformed complex will result in the generation of a signal above background. In this way, test substances which disrupt NHP/intracellular binding partner interaction can be identified.

In a particular embodiment, a NHP fusion can be prepared for immobilization. For example, a NHP or a peptide fragment can be fused to a glutathione-S-transferase (GST) gene using a fusion vector, such as pGEX-5X-1, in such a manner that its binding activity is maintained in the resulting fusion protein. The interactive binding partner can be purified and used to raise a monoclonal antibody, using methods routinely practiced in the art and described above, in Section 5.3. This antibody can be labeled with the radioactive isotope $^{125}$I, for example, by methods routinely practiced in the art. In a heterogeneous assay, e.g., the GST-NHP fusion protein can be anchored to glutathione-agarose beads. The interactive binding partner can then be added in the presence or absence of the test compound in a manner that allows interaction and binding to occur. At the end of the reaction period, unbound material can be washed away, and the labeled monoclonal antibody can be added to the system and allowed to bind to the complexed components. The interaction between a NHP moiety and the interactive binding partner can be detected by measuring the amount of radioactivity that remains associated with the glutathione-agarose beads. A successful inhibition of the interaction by the test compound will result in a decrease in measured radioactivity.

Alternatively, the GST-NHP moiety fusion protein and the interactive binding partner can be mixed together in liquid in the absence of the solid glutathione-agarose beads. The test compound can be added either during or after the species are allowed to interact. This mixture can then be added to the glutathione-agarose beads and unbound material is washed away. Again the extent of inhibition of the NHP moiety/binding partner interaction can be detected by adding the labeled antibody and measuring the radioactivity associated with the beads.

In another embodiment of the invention, these same techniques can be employed using peptide fragments that correspond to the binding domains of a NHP moiety and/or the interactive or binding partner (in cases where the binding partner is a protein), in place of one or both of the full length proteins. Any number of methods routinely practiced in the art can be used to identify and isolate the binding sites. These methods include, but are not limited to, mutagenesis of the gene encoding one of the proteins and screening for disruption of binding in a co-immunoprecipitation assay. Compensatory mutations in the gene encoding the second species in the complex can then be selected. Sequence analysis of the genes encoding the respective proteins will reveal the mutations that correspond to the region of the protein involved in interactive binding. Alternatively, one protein can be anchored to a solid surface using methods described above, and allowed to interact with and bind to its labeled binding partner, which has been treated with a proteolytic enzyme, such as trypsin. After washing, a relatively short, labeled peptide comprising the binding domain may remain associated with the solid material, which can be isolated and identified by amino acid sequencing. Also, once the gene coding for the intracellular binding partner is obtained, short gene segments can be engineered to express peptide fragments of the protein, which can then be tested for binding activity and purified or synthesized.

For example, and not by way of limitation, a NHP moiety can be anchored to a solid material as described, above, by making a GST-NHP moiety fusion protein and allowing it to bind to glutathione agarose beads. The interactive binding partner can be labeled with a radioactive isotope, such as $^{35}S$, and cleaved with a proteolytic enzyme such as trypsin. Cleavage products can then be added to the anchored GST-NHP moiety fusion protein and allowed to bind. After washing away unbound peptides, labeled bound material, representing the intracellular binding partner binding domain, can be eluted, purified, and analyzed for amino acid sequence by well-known methods. Peptides so identified can be produced synthetically or fused to appropriate facilitative proteins using recombinant DNA technology.

6.0. Reference to Microorganism Deposits

The following plasmid has been deposited at the American Type Culture Collection (ATCC), Manassas, Va., USA, under the terms of the Budapest Treaty on the International Recognition of the Deposit of Microorganisms for the Purposes of Patent Procedure and Regulations thereunder (Budapest Treaty) and is thus maintained and made available according to the terms of the Budapest Treaty. Availability of such plasmid is not to be construed as a license to practice the invention in contravention of the rights granted under the authority of any government in accordance with its patent laws.

The deposited plasmid has been assigned the indicated ATCC deposit number:

| Plasmid | ATCC No. |
|---|---|
| LEXENZ17D | PTA-503 |

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims. All publications, patents, and patent applications referenced herein are incorporated by reference in their entirety.

What is claimed is:

1. An isolated polynucleotide comprising a first polynucleotide capable of hybridizing to a second polynucleotide in 0.5 M NaHPO$_4$, 7% sodium dodecyl sulfate (SDS), 1 mM EDTA at 65° C. with washing in 0.1×SSC/0.1% SDS at 68° C., wherein the first polynucleotide encodes a polypeptide having lipoxygenase activity and wherein the second polynucleotide is complementary to the entire sequence of a polynucleotide with the sequence of SEQ ID NO:1.

2. A vector comprising the isolated polynucleotide of claim 1.

3. An in vitro host cell comprising the vector of claim 2.

* * * * *

SEQUENCE LISTING

<160> NUMBER OF SEQ ID NOS: 29

<210> SEQ ID NO 1
<211> LENGTH: 2701
<212> TYPE: DNA
<213> ORGANISM: Homo sapiens

<400> SEQUENCE: 1

```
atggcagtgt accgcctgtg tgtgaccact ggtccctacc tgagggccgg cacactggac      60
aacatctctg tcacactggt gggcacgtgt ggtgaaagcc ccaagcagcg gctagatcga     120
atgggcaggg acttcgcccc tggatcggta cagaagtaca aggtgcgttg cacagcggag     180
ctgggtgagc tcttgctgct gcgtgtacac aaggagcgct acgctttctt ccgcaaggac     240
tcttggtact gtagccgcat ctgtgtcacc gaaccggatg gtagtgtatc ccacttcccc     300
tgctatcagt ggattgaagg ctactgcacc gtggagctga ggccaggaac agcaagaact     360
atttgtcagg actctcttcc cctcctcctg gatcacagga cacgggagct ccgggcccga     420
caagaatgct accgctggaa gatctatgcc cctggcttcc cctgcatggt agacgtcaac     480
agctttcagg agatggagtc agacaagaaa tttgccttga caaagacgac aacttgtgta     540
gaccagggtg acagcagtgg gaatcggtac ctgcccggct tccccatgaa aattgacatc     600
ccatccctga tgtacatgga gcccaatgtt cgatactcag ccaccaagac gatctcgctg     660
```

-continued

```
ctcttcaatg ccatccctgc gtccttggga atgaagcttc gagggctgtt ggatcgcaag      720
ggctcctgga agaagctgga tgacatgcag aacatcttct ggtgccataa gaccttcacg      780
acaaagtatg tcacagagca ctggtgtgaa gatcacttct ttgggtacca gtacctgaat      840
ggtgtcaatc ccgtcatgct ccactgcatc tctagcttgc ccagcaagct gcctgtcacc      900
aatgacatgg tggcccccatt gctgggacag acacatgcc tgcagacaga gctagagagg       960
gggaacatct tcctagcgga ctactggatc ctggcggagg ccccaccca ctgcctaaac      1020 ggccgccagc agtacgtggc cgccccactg tgcctgctgt ggctcagccc caggggggcg     1080
ctggtgccct tggccatcca gctcagccag acccccgggc ctgacagccc catcttcctg     1140
cccactgact ccgaatggga ctggctgctg ccaagacgt gggtgcgcaa ctctgagttc      1200
ctggtgcacg aaaacaacac gcactttctg tgcacgcatt tgctgtgcga ggccttcgcc     1260
atggccacgc tgcgccagct gccgctctgc cacccatct acaagctcct actcccccac      1320
actcgataca cgctgcaggt gaacaccatc gcgagggcca cgctgctcaa ccccgagggc     1380
ctcgtggacc aggtcacgtc catcgggagg caaggcctca tctacctcat gagcacgggc     1440
ctggcccact tcacctacac caatttctgc cttccggaca gctgcgggc ccgcggcgtc      1500 ctggctatcc ccaactacca ctaccgagac gacggcctga agatctgggc ggccattgag     1560
agctttgtct cagaaatcgt gggctactat tatcccagtg acgcatcgt gcagcaggat      1620 tcggagctgc aggcctggac tggcgagatt tttgctcagg cgttcctggg ccgggaaagc     1680 tcaggttttcc caagccggct gtgcacccca ggagagatgg tgaagttcct cactgcaatc     1740
atcttcaatt gctctgccca gcacgctgct gtcaacagtg ggcagcatga ctttggggcc     1800
tggatgccca atgctccatc atccatgagg cagcccccac cccagaccaa ggggaccacc     1860
accctgaaga cttacctaga caccctccct gaagtgaaca tcagctgtaa caacctcctc     1920
ctcttctggt tggttagcca agaacccaag gaccagaggc ccctgggcac ctacccagat     1980
gagcacttca cagaggaggc cccgaggcgg agcatcgccg ccttccagag ccgcctggcc     2040
cagatctcaa gggacatcca ggagcggaac caggggtctgg cactgcccta cacctacctg     2100
gaccctcccc tcattgagaa cagcgtctcc atctaaccac cccaaaatac cacccaagaa     2160
gaaagaaagg tccaagcatg aggaggacca gttcctcagg tcctccagac ccttccatcc     2220
tccctgttct cagttcacct gaaccttctc ttctgcacat ggagactttt gcagccaaga     2280
tggctctgac atcatacaaa ctgggccctg agctgtgaga gaccagcaca gcagcgtcca     2340
ggttaaaagc cgctgaccaa agtccaatgc acaatagccc ctccgaaagg aaggaaccgc     2400
ttcacttctt gccccacttg gggcagcctc ttgttccagc ctcttggaat gcccagcttg     2460
ggtttctgag ctttctccc tcatcctccc caatccccaa actccttctc ctaccatgcc      2520
tttctacgtt ctctttcttc caagcctaga gccaccagcc cagcttcctt ctctggaaaa     2580
gcctggaaac tgggcacaga aggactgtgt gcctggctaa catgtggtcc cctttgtccc     2640
tagcaccttt aagggagggg gaagaattgg agggcagctt gcctggaccc ctaacggctg     2700
t                                                                     2701
```

<210> SEQ ID NO 2
<211> LENGTH: 711
<212> TYPE: PRT
<213> ORGANISM: Homo sapiens

<400> SEQUENCE: 2

Met Ala Val Tyr Arg Leu Cys Val Thr Thr Gly Pro Tyr Leu Arg Ala

```
              1               5              10              15

Gly Thr Leu Asp Asn Ile Ser Val Thr Leu Val Gly Thr Cys Gly Glu
                20              25              30

Ser Pro Lys Gln Arg Leu Asp Arg Met Gly Arg Asp Phe Ala Pro Gly
                35              40              45

Ser Val Gln Lys Tyr Lys Val Arg Cys Thr Ala Glu Leu Gly Glu Leu
                50              55              60

Leu Leu Leu Arg Val His Lys Glu Arg Tyr Ala Phe Phe Arg Lys Asp
65                              70              75              80

Ser Trp Tyr Cys Ser Arg Ile Cys Val Thr Glu Pro Asp Gly Ser Val
                    85              90              95

Ser His Phe Pro Cys Tyr Gln Trp Ile Glu Gly Tyr Cys Thr Val Glu
                100             105             110

Leu Arg Pro Gly Thr Ala Arg Thr Ile Cys Gln Asp Ser Leu Pro Leu
                115             120             125

Leu Leu Asp His Arg Thr Arg Glu Leu Arg Ala Arg Gln Glu Cys Tyr
                130             135             140

Arg Trp Lys Ile Tyr Ala Pro Gly Phe Pro Cys Met Val Asp Val Asn
145                 150             155                         160

Ser Phe Gln Glu Met Glu Ser Asp Lys Lys Phe Ala Leu Thr Lys Thr
                    165             170             175

Thr Thr Cys Val Asp Gln Gly Asp Ser Ser Gly Asn Arg Tyr Leu Pro
                180             185             190

Gly Phe Pro Met Lys Ile Asp Ile Pro Ser Leu Met Tyr Met Glu Pro
                195             200             205

Asn Val Arg Tyr Ser Ala Thr Lys Thr Ile Ser Leu Leu Phe Asn Ala
210                 215             220

Ile Pro Ala Ser Leu Gly Met Lys Leu Arg Gly Leu Leu Asp Arg Lys
225                 230             235                         240

Gly Ser Trp Lys Lys Leu Asp Asp Met Gln Asn Ile Phe Trp Cys His
                    245             250             255

Lys Thr Phe Thr Thr Lys Tyr Val Thr Glu His Trp Cys Glu Asp His
                260             265             270

Phe Phe Gly Tyr Gln Tyr Leu Asn Gly Val Asn Pro Val Met Leu His
                275             280             285

Cys Ile Ser Ser Leu Pro Ser Lys Leu Pro Val Thr Asn Asp Met Val
290                 295             300

Ala Pro Leu Leu Gly Gln Asp Thr Cys Leu Gln Thr Glu Leu Glu Arg
305                 310             315                         320

Gly Asn Ile Phe Leu Ala Asp Tyr Trp Ile Leu Ala Glu Ala Pro Thr
                325             330             335

His Cys Leu Asn Gly Arg Gln Gln Tyr Val Ala Ala Pro Leu Cys Leu
                340             345             350

Leu Trp Leu Ser Pro Gln Gly Ala Leu Val Pro Leu Ala Ile Gln Leu
                355             360             365

Ser Gln Thr Pro Gly Pro Asp Ser Pro Ile Phe Leu Pro Thr Asp Ser
                370             375             380

Glu Trp Asp Trp Leu Leu Ala Lys Thr Trp Val Arg Asn Ser Glu Phe
385                 390             395                         400

Leu Val His Glu Asn Asn Thr His Phe Leu Cys Thr His Leu Leu Cys
                    405             410             415

Glu Ala Phe Ala Met Ala Thr Leu Arg Gln Leu Pro Leu Cys His Pro
                420             425             430
```

```
Ile Tyr Lys Leu Leu Leu Pro His Thr Arg Tyr Thr Leu Gln Val Asn
        435                 440                 445

Thr Ile Ala Arg Ala Thr Leu Leu Asn Pro Glu Gly Leu Val Asp Gln
    450                 455                 460

Val Thr Ser Ile Gly Arg Gln Gly Leu Ile Tyr Leu Met Ser Thr Gly
465                 470                 475                 480

Leu Ala His Phe Thr Tyr Thr Asn Phe Cys Leu Pro Asp Ser Leu Arg
                485                 490                 495

Ala Arg Gly Val Leu Ala Ile Pro Asn Tyr His Tyr Arg Asp Asp Gly
            500                 505                 510

Leu Lys Ile Trp Ala Ala Ile Glu Ser Phe Val Ser Glu Ile Val Gly
        515                 520                 525

Tyr Tyr Pro Ser Asp Ala Ser Val Gln Gln Asp Ser Glu Leu Gln
    530                 535                 540

Ala Trp Thr Gly Glu Ile Phe Ala Gln Ala Phe Leu Gly Arg Glu Ser
545                 550                 555                 560

Ser Gly Phe Pro Ser Arg Leu Cys Thr Pro Gly Glu Met Val Lys Phe
                565                 570                 575

Leu Thr Ala Ile Ile Phe Asn Cys Ser Ala Gln His Ala Ala Val Asn
            580                 585                 590

Ser Gly Gln His Asp Phe Gly Ala Trp Met Pro Asn Ala Pro Ser Ser
        595                 600                 605

Met Arg Gln Pro Pro Pro Gln Thr Lys Gly Thr Thr Thr Leu Lys Thr
    610                 615                 620

Tyr Leu Asp Thr Leu Pro Glu Val Asn Ile Ser Cys Asn Asn Leu Leu
625                 630                 635                 640

Leu Phe Trp Leu Val Ser Gln Glu Pro Lys Asp Gln Arg Pro Leu Gly
                645                 650                 655

Thr Tyr Pro Asp Glu His Phe Thr Glu Glu Ala Pro Arg Arg Ser Ile
            660                 665                 670

Ala Ala Phe Gln Ser Arg Leu Ala Gln Ile Ser Arg Asp Ile Gln Glu
        675                 680                 685

Arg Asn Gln Gly Leu Ala Leu Pro Tyr Thr Tyr Leu Asp Pro Pro Leu
    690                 695                 700

Ile Glu Asn Ser Val Ser Ile
705                 710

<210> SEQ ID NO 3
<211> LENGTH: 1470
<212> TYPE: DNA
<213> ORGANISM: Homo sapiens

<400> SEQUENCE: 3
atggcagtgt accgcctgtg tgtgaccact ggtccctacc tgagggccgg cacactggac      60
aacatctctg tcacactggt gggcacgtgt ggtgaaagcc ccaagcagcg gctagatcga     120
atgggcaggg acttcgcccc tggatcggta cagaagtaca aggtgcgttg cacagcggag     180
ctgggtgagc tcttgctgct gcgtgtacac aaggagcgct acgctttctt ccgcaaggac     240
tcttggtact gtagccgcat ctgtgtcacc gaaccggatg gtagtgtatc ccacttcccc     300
tgctatcagt ggattgaagg ctactgcacc gtggagctga ggccaggaac agcaagaact     360
atttgtcagg actctcttcc cctcctcctg gatcacagga cacgggagct ccgggcccga     420
caagaatgct accgctggaa gatctatgcc cctggcttcc cctgcatggt agacgtcaac     480
```

```
agctttcagg agatggagtc agacaagaaa tttgccttga caaagacgac aacttgtgta      540
gaccagggtg acagcagtgg gaatcggtac ctgcccggct tccccatgaa aattgacatc      600
ccatccctga tgtacatgga gcccaatgtt cgatactcag ccaccaagac gatctcgctg      660
ctcttcaatg ccatccctgc gtccttggga atgaagcttc gagggctgtt ggatcgcaag      720
ggctcctgga agaagctgga tgacatgcag aacatcttct ggtgccataa gaccttcacg      780
acaaagtatg tcacagagca ctggtgtgaa gatcacttct ttgggtacca gtacctgaat      840
ggtgtcaatc ccgtcatgct ccactgcatc tctagcttgc ccagcaagct gcctgtcacc      900
aatgacatgg tggcccccctt gctgggacag gacacatgcc tgcagacaga gctagagagg      960
gggaacatct tcctagcgga ctactggatc ctggcggagg ccccacccca ctgcctaaac     1020
ggccgccagc agtacgtggc cgccccactg tgcctgctgt ggctcagccc caggggggcg     1080
ctggtgccct tggccatcca gctcagccag accccgggc ctgacagccc catcttcctg      1140
cccactgact ccgaatggga ctggctgctg gccaagacgt gggtgcgcaa ctctgagttc     1200
ctggtgcacg aaaacaacac gcactttctg tgcacgcatt tgctgtgcga ggccttcgcc     1260
atggccacgc tgcgccagct gccgctctgc cacccccatct acaagctcct actcccccac     1320
actcgataca cgctgcaggt gaacaccatc gcgagggcca cgctgctcaa ccccgagggc     1380
ctcgtggacc agcctgcggg cccgcggcgt cctggctatc cccaactacc actaccgaga     1440
cgacggcctg aagatctggg cggccattga                                       1470

<210> SEQ ID NO 4
<211> LENGTH: 489
<212> TYPE: PRT
<213> ORGANISM: Homo sapiens

<400> SEQUENCE: 4

Met Ala Val Tyr Arg Leu Cys Val Thr Thr Gly Pro Tyr Leu Arg Ala
  1               5                  10                  15

Gly Thr Leu Asp Asn Ile Ser Val Thr Leu Val Gly Thr Cys Gly Glu
             20                  25                  30

Ser Pro Lys Gln Arg Leu Asp Arg Met Gly Arg Asp Phe Ala Pro Gly
         35                  40                  45

Ser Val Gln Lys Tyr Lys Val Arg Cys Thr Ala Glu Leu Gly Glu Leu
     50                  55                  60

Leu Leu Leu Arg Val His Lys Glu Arg Tyr Ala Phe Phe Arg Lys Asp
 65                  70                  75                  80

Ser Trp Tyr Cys Ser Arg Ile Cys Val Thr Glu Pro Asp Gly Ser Val
                 85                  90                  95

Ser His Phe Pro Cys Tyr Gln Trp Ile Glu Gly Tyr Cys Thr Val Glu
            100                 105                 110

Leu Arg Pro Gly Thr Ala Arg Thr Ile Cys Gln Asp Ser Leu Pro Leu
        115                 120                 125

Leu Leu Asp His Arg Thr Arg Glu Leu Arg Ala Arg Gln Glu Cys Tyr
    130                 135                 140

Arg Trp Lys Ile Tyr Ala Pro Gly Phe Pro Cys Met Val Asp Val Asn
145                 150                 155                 160

Ser Phe Gln Glu Met Glu Ser Asp Lys Lys Phe Ala Leu Thr Lys Thr
                165                 170                 175

Thr Thr Cys Val Asp Gln Gly Asp Ser Ser Gly Asn Arg Tyr Leu Pro
            180                 185                 190

Gly Phe Pro Met Lys Ile Asp Ile Pro Ser Leu Met Tyr Met Glu Pro
```

-continued

```
              195                 200                 205
Asn Val Arg Tyr Ser Ala Thr Lys Thr Ile Ser Leu Leu Phe Asn Ala
            210                 215                 220
Ile Pro Ala Ser Leu Gly Met Lys Leu Arg Gly Leu Leu Asp Arg Lys
225                 230                 235                 240
Gly Ser Trp Lys Lys Leu Asp Asp Met Gln Asn Ile Phe Trp Cys His
                245                 250                 255
Lys Thr Phe Thr Thr Lys Tyr Val Thr Glu His Trp Cys Glu Asp His
            260                 265                 270
Phe Phe Gly Tyr Gln Tyr Leu Asn Gly Val Asn Pro Val Met Leu His
            275                 280                 285
Cys Ile Ser Ser Leu Pro Ser Lys Leu Pro Val Thr Asn Asp Met Val
            290                 295                 300
Ala Pro Leu Leu Gly Gln Asp Thr Cys Leu Gln Thr Glu Leu Glu Arg
305                 310                 315                 320
Gly Asn Ile Phe Leu Ala Asp Tyr Trp Ile Leu Ala Glu Ala Pro Thr
                325                 330                 335
His Cys Leu Asn Gly Arg Gln Gln Tyr Val Ala Ala Pro Leu Cys Leu
                340                 345                 350
Leu Trp Leu Ser Pro Gln Gly Ala Leu Val Pro Leu Ala Ile Gln Leu
            355                 360                 365
Ser Gln Thr Pro Gly Pro Asp Ser Pro Ile Phe Leu Pro Thr Asp Ser
            370                 375                 380
Glu Trp Asp Trp Leu Leu Ala Lys Thr Trp Val Arg Asn Ser Glu Phe
385                 390                 395                 400
Leu Val His Glu Asn Asn Thr His Phe Leu Cys Thr His Leu Leu Cys
                405                 410                 415
Glu Ala Phe Ala Met Ala Thr Leu Arg Gln Leu Pro Leu Cys His Pro
                420                 425                 430
Ile Tyr Lys Leu Leu Pro His Thr Arg Tyr Thr Leu Gln Val Asn
            435                 440                 445
Thr Ile Ala Arg Ala Thr Leu Leu Asn Pro Glu Gly Leu Val Asp Gln
            450                 455                 460
Pro Ala Gly Pro Arg Arg Pro Gly Tyr Pro Gln Leu Pro Leu Pro Arg
465                 470                 475                 480
Arg Arg Pro Glu Asp Leu Gly Gly His
                485
```

<210> SEQ ID NO 5
<211> LENGTH: 2236
<212> TYPE: DNA
<213> ORGANISM: Homo sapiens

<400> SEQUENCE: 5

| | | | | | |
|---|---|---|---|---|---|
| atggtagacg | tcaacagctt | tcaggagatg | gagtcagaca | agaaatttgc | cttgacaaag | 60 |
| acgacaactt | gtgtagacca | gggtgacagc | agtgggaatc | ggtacctgcc | cggcttcccc | 120 |
| atgaaaattg | acatcccatc | cctgatgtac | atggagccca | atgttcgata | tcagccacc | 180 |
| aagacgatct | cgctgctctt | caatgccatc | cctgcgtcct | gggaatgaa | gcttcgaggg | 240 |
| ctgttggatc | gcaagggctc | ctggaagaag | ctggatgaca | tgcagaacat | cttctggtgc | 300 |
| cataagacct | tcacgacaaa | gtatgtcaca | gagcactggt | gtgaagatca | cttctttggg | 360 |
| taccagtacc | tgaatggtgt | caatcccgtc | atgctccact | gcatctctag | cttgcccagc | 420 |
| aagctgcctg | tcaccaatga | catggtggcc | cccttgctgg | gacaggacac | atgcctgcag | 480 |

-continued

```
acagagctag agaggggaa catcttccta gcggactact ggatcctggc ggaggccccc      540
acccactgcc taaacggccg ccagcagtac gtggccgccc cactgtgcct gctgtggctc      600
agccccagg gggcgctggt gcccttggcc atccagctca ccagaccccc cgggcctgac      660
agccccatct tcctgccaac tgactccgaa tgggactggc tgctggccaa gacgtgggtg      720
cgcaactctg agttcctggt gcacgaaaac aacacgcact ttctgtgcac gcatttgctg      780
tgcgaggcct tcgccatggc cacgctgcgc cagctgccgc tctgccaccc catctacaag      840
ctcctactcc cccacactcg atacacgctg caggtgaaca ccatcgcgag gccacgctg      900
ctcaaccccg agggcctcgt ggaccaggtc acgtccatcg ggaggcaagg cctcatctac      960
ctcatgagca cgggcctggc ccacttcacc tacaccaatt ctgccttcc ggacagcctg      1020
cgggcccgcg gcgtcctggc tatccccaac taccactacc gagacgacgg cctgaagatc      1080
tgggcggcca ttgagagctt tgtctcagaa atcgtgggct actattatcc cagtgacgca      1140
tctgtgcagc aggattcgga gctgcaggcc tggactggcg agattttgc tcaggcgttc      1200
ctgggccggg aaagctcagg tttcccaagc cggctgtgca ccccaggaga gatggtgaag      1260
ttcctcactg caatcatctt caattgctct gcccagcacg ctgctgtcaa cagtgggcag      1320
catgactttg gggcctggat gcccaatgct ccatcatcca tgaggcagcc cccaccccag      1380
accaaggga ccaccaccct gaagacttac ctagacaccc tccctgaagt gaacatcagc      1440
tgtaacaacc tcctcctctt ctggttggtt agccaagaac ccaaggacca gaggcccctg      1500
ggcacctacc cagatgagca cttcacagag gaggccccga ggcggagcat cgccgccttc      1560
cagagccgcc tggcccagat ctcaaggaac atccaggagc ggaaccaggg tctggcactg      1620
ccctacacct acctggaccc tccctcatt gagaacagcc tctccatcta accacccca       1680
aataccaccc aagaagaaag aaaggtccaa gcatgaggag gaccagttcc tcaggtcctc      1740
cagacccttc catcctcct gttctcagtt cacctgaacc ttctcttctg cacatggaga      1800
cttttgcagc caagatggct ctgacatcat acaaactggg ccctgagctg tgagagacca      1860
gcacagcagc gtccaggtta aaagccgctg accaaagtcc aatgcacaat agcccctccg      1920
aaaggaagga accgcttcac ttcttgcccc acttgggca gcctcttgtt ccagcctctt      1980
ggaatgccca gcttgggttt ctgagctttt ctccctcatc ctccccaatc ccaaactcc      2040
ttctcctacc atgcctttct acgttctctt tcttccaagc ctagagccac cagcccagct      2100
tccttctctg gaaaagcctg gaaactgggc acagaaggac tgtgtgcctg ctaacatgt      2160
ggtcccctt gtccctagca cctttaaggg gagggaaga attggagggc agcttgcctg      2220
gaccccctaac ggctgt                                                     2236
```

<210> SEQ ID NO 6
<211> LENGTH: 556
<212> TYPE: PRT
<213> ORGANISM: Homo sapiens

<400> SEQUENCE: 6

Met Val Asp Val Asn Ser Phe Gln Glu Met Glu Ser Asp Lys Lys Phe
 1               5                  10                  15

Ala Leu Thr Lys Thr Thr Thr Cys Val Asp Gln Gly Asp Ser Ser Gly
             20                  25                  30

Asn Arg Tyr Leu Pro Gly Phe Pro Met Lys Ile Asp Ile Pro Ser Leu
         35                  40                  45

Met Tyr Met Glu Pro Asn Val Arg Tyr Ser Ala Thr Lys Thr Ile Ser

-continued

```
                50                  55                  60
Leu Leu Phe Asn Ala Ile Pro Ala Ser Leu Gly Met Lys Leu Arg Gly
 65                  70                  75                  80

Leu Leu Asp Arg Lys Gly Ser Trp Lys Lys Leu Asp Asp Met Gln Asn
                 85                  90                  95

Ile Phe Trp Cys His Lys Thr Phe Thr Thr Lys Tyr Val Thr Glu His
                100                 105                 110

Trp Cys Glu Asp His Phe Phe Gly Tyr Gln Tyr Leu Asn Gly Val Asn
                115                 120                 125

Pro Val Met Leu His Cys Ile Ser Ser Leu Pro Ser Lys Leu Pro Val
                130                 135                 140

Thr Asn Asp Met Val Ala Pro Leu Leu Gly Gln Asp Thr Cys Leu Gln
145                 150                 155                 160

Thr Glu Leu Glu Arg Gly Asn Ile Phe Leu Ala Asp Tyr Trp Ile Leu
                165                 170                 175

Ala Glu Ala Pro Thr His Cys Leu Asn Gly Arg Gln Gln Tyr Val Ala
                180                 185                 190

Ala Pro Leu Cys Leu Leu Trp Leu Ser Pro Gln Gly Ala Leu Val Pro
                195                 200                 205

Leu Ala Ile Gln Leu Ser Gln Thr Pro Gly Pro Asp Ser Pro Ile Phe
210                 215                 220

Leu Pro Thr Asp Ser Glu Trp Asp Trp Leu Leu Ala Lys Thr Trp Val
225                 230                 235                 240

Arg Asn Ser Glu Phe Leu Val His Glu Asn Asn Thr His Phe Leu Cys
                245                 250                 255

Thr His Leu Leu Cys Glu Ala Phe Ala Met Ala Thr Leu Arg Gln Leu
                260                 265                 270

Pro Leu Cys His Pro Ile Tyr Lys Leu Leu Pro His Thr Arg Tyr
                275                 280                 285

Thr Leu Gln Val Asn Thr Ile Ala Arg Ala Thr Leu Leu Asn Pro Glu
                290                 295                 300

Gly Leu Val Asp Gln Val Thr Ser Ile Gly Arg Gln Gly Leu Ile Tyr
305                 310                 315                 320

Leu Met Ser Thr Gly Leu Ala His Phe Thr Tyr Thr Asn Phe Cys Leu
                325                 330                 335

Pro Asp Ser Leu Arg Ala Arg Gly Val Leu Ala Ile Pro Asn Tyr His
                340                 345                 350

Tyr Arg Asp Asp Gly Leu Lys Ile Trp Ala Ala Ile Glu Ser Phe Val
                355                 360                 365

Ser Glu Ile Val Gly Tyr Tyr Tyr Pro Ser Asp Ala Ser Val Gln Gln
370                 375                 380

Asp Ser Glu Leu Gln Ala Trp Thr Gly Glu Ile Phe Ala Gln Ala Phe
385                 390                 395                 400

Leu Gly Arg Glu Ser Ser Gly Phe Pro Ser Arg Leu Cys Thr Pro Gly
                405                 410                 415

Glu Met Val Lys Phe Leu Thr Ala Ile Ile Phe Asn Cys Ser Ala Gln
                420                 425                 430

His Ala Ala Val Asn Ser Gly Gln His Asp Phe Gly Ala Trp Met Pro
                435                 440                 445

Asn Ala Pro Ser Ser Met Arg Gln Pro Pro Gln Thr Lys Gly Thr
                450                 455                 460

Thr Thr Leu Lys Thr Tyr Leu Asp Thr Leu Pro Glu Val Asn Ile Ser
465                 470                 475                 480
```

-continued

Cys Asn Asn Leu Leu Leu Phe Trp Leu Val Ser Gln Glu Pro Lys Asp
              485                 490                 495

Gln Arg Pro Leu Gly Thr Tyr Pro Asp Glu His Phe Thr Glu Glu Ala
            500                 505                 510

Pro Arg Ser Ile Ala Ala Phe Gln Ser Arg Leu Ala Gln Ile Ser
            515                 520                 525

Arg Asp Ile Gln Glu Arg Asn Gln Gly Leu Ala Leu Pro Tyr Thr Tyr
            530                 535                 540

Leu Asp Pro Pro Leu Ile Glu Asn Ser Val Ser Ile
545                 550                 555

<210> SEQ ID NO 7
<211> LENGTH: 1005
<212> TYPE: DNA
<213> ORGANISM: Homo sapiens

<400> SEQUENCE: 7
atggtagacg tcaacagctt tcaggagatg gagtcagaca agaaatttgc cttgacaaag        60
acgacaactt gtgtagacca gggtgacagc agtgggaatc ggtacctgcc cggcttcccc       120
atgaaaattg acatcccatc cctgatgtac atggagccca tgttcgata ctcagccacc        180 aagacgatct cgctgctctt caatgccatc cctgcgtcct tgggaatgaa gcttcgaggg       240
ctgttggatc gcaagggctc ctggaagaag ctggatgaca tgcagaacat cttctggtgc       300
cataagacct tcacgacaaa gtatgtcaca gagcactggt gtgaagatca cttctttggg       360
taccagtacc tgaatggtgt caatcccgtc atgctccact gcatctctag cttgcccagc       420
aagctgcctg tcaccaatga catggtggcc cccttgctgg acaggacac atgcctgcag         480 acagagctag agagggggaa catcttccta gcggactact ggatcctggc ggaggccccc       540
acccactgcc taaacggccg ccagcagtac gtggccgccc cactgtgcct gctgtggctc       600
agcccccagg gggcgctggt gcccttggcc atccagctca gccagacccc cgggcctgac       660
agccccatct tcctgcccac tgactccgaa tgggactggc tgctggccaa gacgtgggtg       720
cgcaactctg agttcctggt gcacgaaaac aacacgcact ttctgtgcac gcatttgctg       780
tgcgaggcct tcgccatggc cacgctgcgc cagctgccgc tctgccaccc catctacaag       840
ctcctactcc cccacactcg atacacgctg caggtgaaca ccatcgcgag ggccacgctg       900
ctcaaccccg agggcctcgt ggaccagcct gcgggcccgc ggcgtcctgg ctatccccaa       960
ctaccactac cgagacgacg gcctgaagat ctgggcggcc attga                       1005

<210> SEQ ID NO 8
<211> LENGTH: 334
<212> TYPE: PRT
<213> ORGANISM: Homo sapiens

<400> SEQUENCE: 8

Met Val Asp Val Asn Ser Phe Gln Glu Met Glu Ser Asp Lys Lys Phe
1               5                   10                  15

Ala Leu Thr Lys Thr Thr Thr Cys Val Asp Gln Gly Asp Ser Ser Gly
            20                  25                  30

Asn Arg Tyr Leu Pro Gly Phe Pro Met Lys Ile Asp Ile Pro Ser Leu
            35                  40                  45

Met Tyr Met Glu Pro Asn Val Arg Tyr Ser Ala Thr Lys Thr Ile Ser
        50                  55                  60

Leu Leu Phe Asn Ala Ile Pro Ala Ser Leu Gly Met Lys Leu Arg Gly

```
                65                  70                  75                  80
Leu Leu Asp Arg Lys Gly Ser Trp Lys Lys Leu Asp Asp Met Gln Asn
                    85                  90                  95

Ile Phe Trp Cys His Lys Thr Phe Thr Thr Lys Tyr Val Thr Glu His
                100                 105                 110

Trp Cys Glu Asp His Phe Phe Gly Tyr Gln Tyr Leu Asn Gly Val Asn
                115                 120                 125

Pro Val Met Leu His Cys Ile Ser Ser Leu Pro Ser Lys Leu Pro Val
            130                 135                 140

Thr Asn Asp Met Val Ala Pro Leu Leu Gly Gln Asp Thr Cys Leu Gln
145                 150                 155                 160

Thr Glu Leu Glu Arg Gly Asn Ile Phe Leu Ala Asp Tyr Trp Ile Leu
                165                 170                 175

Ala Glu Ala Pro Thr His Cys Leu Asn Gly Arg Gln Gln Tyr Val Ala
                180                 185                 190

Ala Pro Leu Cys Leu Leu Trp Leu Ser Pro Gln Gly Ala Leu Val Pro
            195                 200                 205

Leu Ala Ile Gln Leu Ser Gln Thr Pro Gly Pro Asp Ser Pro Ile Phe
        210                 215                 220

Leu Pro Thr Asp Ser Glu Trp Asp Trp Leu Leu Ala Lys Thr Trp Val
225                 230                 235                 240

Arg Asn Ser Glu Phe Leu Val His Glu Asn Asn Thr His Phe Leu Cys
                245                 250                 255

Thr His Leu Leu Cys Glu Ala Phe Ala Met Ala Thr Leu Arg Gln Leu
            260                 265                 270

Pro Leu Cys His Pro Ile Tyr Lys Leu Leu Pro His Thr Arg Tyr
        275                 280                 285

Thr Leu Gln Val Asn Thr Ile Ala Arg Ala Thr Leu Leu Asn Pro Glu
        290                 295                 300

Gly Leu Val Asp Gln Pro Ala Gly Pro Arg Pro Gly Tyr Pro Gln
305                 310                 315                 320

Leu Pro Leu Pro Arg Arg Pro Glu Asp Leu Gly Gly His
                325                 330
```

<210> SEQ ID NO 9
<211> LENGTH: 1848
<212> TYPE: DNA
<213> ORGANISM: Homo sapiens

<400> SEQUENCE: 9

```
atggcagtgt accgcctgtg tgtgaccact ggtccctacc tgagggccgg cacactggac    60
aacatctctg tcacactggt gggcacgtgt ggtgaaagcc ccaagcagcg gctagatcga   120
atgggcaggg acttcgcccc tggatcggta cagaagtaca aggtgcgttg cacagcggag   180
ctgggtgagc tcttgctgct gcgtgtacac aaggagcgca cgctttctt ccgcaaggac   240
tcttggtact gtagccgcat ctgtgtcacc gaaccggatg gtagtgtatc ccacttcccc   300
tgctatcagt ggattgaagg ctactgcacc gtggagctga ggccaggaac agcaagaact   360
atttgtcagg actctcttcc cctcctcctg gatcacagga cgggagct ccgggcccga   420
caagaatgct accgctggaa gatctatgcc cctggcttcc cctgcatggt agacgtcaac   480
agctttcagg agatggagtc agacaagaaa tttgccttga caaagacgac aacttgtgta   540
gaccagggtg acagcagtgg gaatcggtac ctgcccggct tccccatgaa aattgacatc   600
ccatccctga tgtacatgga gcccaatgtt cgatactcag ccaccaagac gatctcgctg   660
```

-continued

```
ctcttcaatg ccatccctgc gtccttggga atgaagcttc gagggctgtt ggatcgcaag      720
ggctcctgga agaagctgga tgacatgcag aacatcttct ggtgccataa gaccttcacg      780
acaaagtatg tcacagagca ctggtgtgaa gatcacttct ttgggtacca gtacctgaat      840
ggtgtcaatc ccgtcatgct ccactgcatc tctagcttgc ccagcaagct gcctgtcacc      900
aatgacatgg tggccccctt gctgggacag gacacatgcc tgcagacaga gctagagagg      960
gggaacatct tcctagcgga ctactggatc ctggcggagg ccccacccca ctgcctaaac     1020
ggccgccagc agtacgtggc cgccccactg tgcctgctgt ggctcagccc caggggggcg     1080
ctggtgccct tggccatcca gctcagccag accccgggc ctgacagccc catcttcctg      1140
cccactgact ccgaatggga ctggctgctg gccaagacgt gggtgcgcaa ctctgagttc     1200
ctggtgcacg aaaacaacac gcactttctg tgcacgcatt tgctgtgcga ggccttcgcc     1260
atggccacgc tgcgccagct gccgctctgc caccccatct acaagctcct actccccac     1320 actcgataca cgctgcaggt gaacaccatc gcgagggcca cgctgctcaa ccccgagggc     1380
ctcgtggacc aggtcacgtc catcggagg caaggcctca tctacctcat gagcacgggc     1440
ctggcccact tcacctacac caatttctgc cttccggaca gcctgcgggc ccgcggcgtc     1500
ctggctatcc ccaactacca ctaccgagac gacggcctga gatctgggc ggccattgag      1560 agctttgtct cagaaatcgt gggctactat tatcccagtg acgcatctgt gcagcaggat     1620
tcggagctgc aggcctggac tggcgagatt tttgctcagg cgttcctggg ccgggaaagc     1680
tcaggtttcc caagccggct gtgcacccca ggagagatgt gaagttcct cactgcaatc      1740 atcttcaatt gctctgccca gcacgctgct gtcaacagtg ggcaggacgg cagaggtgga     1800
atcagggatg gtgaagaggg aggtgatact ccccttctgg ccaactga                  1848
```

<210> SEQ ID NO 10
<211> LENGTH: 615
<212> TYPE: PRT
<213> ORGANISM: Homo sapiens

<400> SEQUENCE: 10

```
Met Ala Val Tyr Arg Leu Cys Val Thr Thr Gly Pro Tyr Leu Arg Ala
 1               5                  10                  15

Gly Thr Leu Asp Asn Ile Ser Val Thr Leu Val Gly Thr Cys Gly Glu
            20                  25                  30

Ser Pro Lys Gln Arg Leu Asp Arg Met Gly Arg Asp Phe Ala Pro Gly
        35                  40                  45

Ser Val Gln Lys Tyr Lys Val Arg Cys Thr Ala Glu Leu Gly Glu Leu
    50                  55                  60

Leu Leu Leu Arg Val His Lys Glu Arg Tyr Ala Phe Phe Arg Lys Asp
65                  70                  75                  80

Ser Trp Tyr Cys Ser Arg Ile Cys Val Thr Glu Pro Asp Gly Ser Val
                85                  90                  95

Ser His Phe Pro Cys Tyr Gln Trp Ile Glu Gly Tyr Cys Thr Val Glu
            100                 105                 110

Leu Arg Pro Gly Thr Ala Arg Thr Ile Cys Gln Asp Ser Leu Pro Leu
        115                 120                 125

Leu Leu Asp His Arg Thr Arg Glu Leu Arg Ala Arg Gln Glu Cys Tyr
    130                 135                 140

Arg Trp Lys Ile Tyr Ala Pro Gly Phe Pro Cys Met Val Asp Val Asn
145                 150                 155                 160
```

-continued

```
Ser Phe Gln Glu Met Glu Ser Asp Lys Lys Phe Ala Leu Thr Lys Thr
                165                 170                 175
Thr Thr Cys Val Asp Gln Gly Asp Ser Ser Gly Asn Arg Tyr Leu Pro
            180                 185                 190
Gly Phe Pro Met Lys Ile Asp Ile Pro Ser Leu Met Tyr Met Glu Pro
        195                 200                 205
Asn Val Arg Tyr Ser Ala Thr Lys Thr Ile Ser Leu Leu Phe Asn Ala
    210                 215                 220
Ile Pro Ala Ser Leu Gly Met Lys Leu Arg Gly Leu Leu Asp Arg Lys
225                 230                 235                 240
Gly Ser Trp Lys Lys Leu Asp Asp Met Gln Asn Ile Phe Trp Cys His
                245                 250                 255
Lys Thr Phe Thr Thr Lys Tyr Val Thr Glu His Trp Cys Glu Asp His
            260                 265                 270
Phe Phe Gly Tyr Gln Tyr Leu Asn Gly Val Asn Pro Val Met Leu His
        275                 280                 285
Cys Ile Ser Ser Leu Pro Ser Lys Leu Pro Val Thr Asn Asp Met Val
    290                 295                 300
Ala Pro Leu Leu Gly Gln Asp Thr Cys Leu Gln Thr Glu Leu Glu Arg
305                 310                 315                 320
Gly Asn Ile Phe Leu Ala Asp Tyr Trp Ile Leu Ala Glu Ala Pro Thr
                325                 330                 335
His Cys Leu Asn Gly Arg Gln Gln Tyr Val Ala Ala Pro Leu Cys Leu
            340                 345                 350
Leu Trp Leu Ser Pro Gln Gly Ala Leu Val Pro Leu Ala Ile Gln Leu
        355                 360                 365
Ser Gln Thr Pro Gly Pro Asp Ser Pro Ile Phe Leu Pro Thr Asp Ser
    370                 375                 380
Glu Trp Asp Trp Leu Leu Ala Lys Thr Trp Val Arg Asn Ser Glu Phe
385                 390                 395                 400
Leu Val His Glu Asn Asn Thr His Phe Leu Cys Thr His Leu Leu Cys
                405                 410                 415
Glu Ala Phe Ala Met Ala Thr Leu Arg Gln Leu Pro Leu Cys His Pro
            420                 425                 430
Ile Tyr Lys Leu Leu Leu Pro His Thr Arg Tyr Thr Leu Gln Val Asn
        435                 440                 445
Thr Ile Ala Arg Ala Thr Leu Leu Asn Pro Glu Gly Leu Val Asp Gln
    450                 455                 460
Val Thr Ser Ile Gly Arg Gln Gly Leu Ile Tyr Leu Met Ser Thr Gly
465                 470                 475                 480
Leu Ala His Phe Thr Tyr Thr Asn Phe Cys Leu Pro Asp Ser Leu Arg
                485                 490                 495
Ala Arg Gly Val Leu Ala Ile Pro Asn Tyr His Tyr Arg Asp Asp Gly
            500                 505                 510
Leu Lys Ile Trp Ala Ala Ile Glu Ser Phe Val Ser Glu Ile Val Gly
        515                 520                 525
Tyr Tyr Tyr Pro Ser Asp Ala Ser Val Gln Asp Ser Glu Leu Gln
    530                 535                 540
Ala Trp Thr Gly Glu Ile Phe Ala Gln Ala Phe Leu Gly Arg Glu Ser
545                 550                 555                 560
Ser Gly Phe Pro Ser Arg Leu Cys Thr Pro Gly Glu Met Val Lys Phe
                565                 570                 575
Leu Thr Ala Ile Ile Phe Asn Cys Ser Ala Gln His Ala Ala Val Asn
```

580                 585                 590
    Ser Gly Gln Asp Gly Arg Gly Gly Ile Arg Asp Gly Glu Gly Gly
            595                 600                 605

Asp Thr Pro Leu Leu Ala Asn
        610                 615

<210> SEQ ID NO 11
<211> LENGTH: 1383
<212> TYPE: DNA
<213> ORGANISM: Homo sapiens

<400> SEQUENCE: 11

| | | | | | |
|---|---|---|---|---|---|
| atggtagacg | tcaacagctt | tcaggagatg | gagtcagaca | agaaatttgc | cttgacaaag | 60 |
| acgacaactt | gtgtagacca | gggtgacagc | agtgggaatc | ggtacctgcc | cggcttcccc | 120 |
| atgaaaattg | acatcccatc | cctgatgtac | atggagccca | atgttcgata | ctcagccacc | 180 |
| aagacgatct | cgctgctctt | caatgccatc | cctgcgtcct | tgggaatgaa | gcttcgaggg | 240 |
| ctgttggatc | gcaagggctc | ctggaagaag | ctggatgaca | tgcagaacat | cttctggtgc | 300 |
| cataagacct | tcacgacaaa | gtatgtcaca | gagcactggt | gtgaagatca | cttctttggg | 360 |
| taccagtacc | tgaatggtgt | caatcccgtc | atgctccact | gcatctctag | cttgcccagc | 420 |
| aagctgcctg | tcaccaatga | catggtggcc | cccttgctgg | acaggacac | atgcctgcag | 480 |
| acagagctag | agaggggaa | catcttccta | gcggactact | ggatcctggc | ggaggccccc | 540 |
| acccactgcc | taaacggccg | ccagcagtac | gtggccgccc | cactgtgcct | gctgtggctc | 600 |
| agcccccagg | gggcgctggt | gcccttggcc | atccagctca | gccagacccc | cgggcctgac | 660 |
| agccccatct | tcctgcccac | tgactccgaa | tgggactggc | tgctggccaa | gacgtgggtg | 720 |
| cgcaactctg | agttcctggt | gcacgaaaac | aacacgcact | ttctgtgcac | gcatttgctg | 780 |
| tgcgaggcct | tcgccatggc | cacgctgcgc | cagctgccgc | tctgccaccc | catctacaag | 840 |
| ctcctactcc | cccacactcg | atacacgctg | caggtgaaca | ccatcgcgag | ggccacgctg | 900 |
| ctcaaccccg | agggcctcgt | ggaccaggtc | acgtccatcg | ggaggcaagg | cctcatctac | 960 |
| ctcatgagca | cgggcctggc | ccacttcacc | tacaccaatt | tctgccttcc | ggacagcctg | 1020 |
| cgggcccgcg | cgtcctggc | tatccccaac | taccactacc | gagacgacgg | cctgaagatc | 1080 |
| tgggcggcca | ttgagagctt | tgtctcagaa | atcgtgggct | actattatcc | cagtgacgca | 1140 |
| tctgtgcagc | aggattcgga | gctgcaggcc | tggactggcg | agattttttgc | tcaggcgttc | 1200 |
| ctgggccggg | aaagctcagg | tttcccaagc | cggctgtgca | ccccaggaga | gatggtgaag | 1260 |
| ttcctcactg | caatcatctt | caattgctct | gcccagcacg | ctgctgtcaa | cagtgggcag | 1320 |
| gacggcagag | gtggaatcag | ggatggtgaa | gagggaggtg | atactccccct | tctggccaac | 1380 |
| tga | | | | | | 1383 |

<210> SEQ ID NO 12
<211> LENGTH: 460
<212> TYPE: PRT
<213> ORGANISM: Homo sapiens

<400> SEQUENCE: 12

Met Val Asp Val Asn Ser Phe Gln Glu Met Glu Ser Asp Lys Lys Phe
 1                 5                  10                  15

Ala Leu Thr Lys Thr Thr Thr Cys Val Asp Gln Gly Asp Ser Ser Gly
            20                  25                  30

Asn Arg Tyr Leu Pro Gly Phe Pro Met Lys Ile Asp Ile Pro Ser Leu

```
                35                  40                  45
Met Tyr Met Glu Pro Asn Val Arg Tyr Ser Ala Thr Lys Thr Ile Ser
 50                  55                  60

Leu Leu Phe Asn Ala Ile Pro Ala Ser Leu Gly Met Lys Leu Arg Gly
 65                  70                  75                  80

Leu Leu Asp Arg Lys Gly Ser Trp Lys Lys Leu Asp Asp Met Gln Asn
                 85                  90                  95

Ile Phe Trp Cys His Lys Thr Phe Thr Thr Lys Tyr Val Thr Glu His
                100                 105                 110

Trp Cys Glu Asp His Phe Phe Gly Tyr Gln Tyr Leu Asn Gly Val Asn
                115                 120                 125

Pro Val Met Leu His Cys Ile Ser Ser Leu Pro Ser Lys Leu Pro Val
    130                 135                 140

Thr Asn Asp Met Val Ala Pro Leu Leu Gly Gln Asp Thr Cys Leu Gln
145                 150                 155                 160

Thr Glu Leu Glu Arg Gly Asn Ile Phe Leu Ala Asp Tyr Trp Ile Leu
                165                 170                 175

Ala Glu Ala Pro Thr His Cys Leu Asn Gly Arg Gln Gln Tyr Val Ala
                180                 185                 190

Ala Pro Leu Cys Leu Leu Trp Leu Ser Pro Gln Gly Ala Leu Val Pro
                195                 200                 205

Leu Ala Ile Gln Leu Ser Gln Thr Pro Gly Pro Asp Ser Pro Ile Phe
    210                 215                 220

Leu Pro Thr Asp Ser Glu Trp Asp Trp Leu Leu Ala Lys Thr Trp Val
225                 230                 235                 240

Arg Asn Ser Glu Phe Leu Val His Glu Asn Asn Thr His Phe Leu Cys
                245                 250                 255

Thr His Leu Leu Cys Glu Ala Phe Ala Met Ala Thr Leu Arg Gln Leu
                260                 265                 270

Pro Leu Cys His Pro Ile Tyr Lys Leu Leu Pro His Thr Arg Tyr
                275                 280                 285

Thr Leu Gln Val Asn Thr Ile Ala Arg Ala Thr Leu Leu Asn Pro Glu
    290                 295                 300

Gly Leu Val Asp Gln Val Thr Ser Ile Gly Arg Gln Gly Leu Ile Tyr
305                 310                 315                 320

Leu Met Ser Thr Gly Leu Ala His Phe Thr Tyr Thr Asn Phe Cys Leu
                325                 330                 335

Pro Asp Ser Leu Arg Ala Arg Gly Val Leu Ala Ile Pro Asn Tyr His
                340                 345                 350

Tyr Arg Asp Asp Gly Leu Lys Ile Trp Ala Ala Ile Glu Ser Phe Val
                355                 360                 365

Ser Glu Ile Val Gly Tyr Tyr Tyr Pro Ser Asp Ala Ser Val Gln Gln
    370                 375                 380

Asp Ser Glu Leu Gln Ala Trp Thr Gly Glu Ile Phe Ala Gln Ala Phe
385                 390                 395                 400

Leu Gly Arg Glu Ser Ser Gly Phe Pro Ser Arg Leu Cys Thr Pro Gly
                405                 410                 415

Glu Met Val Lys Phe Leu Thr Ala Ile Ile Phe Asn Cys Ser Ala Gln
                420                 425                 430

His Ala Ala Val Asn Ser Gly Gln Asp Gly Arg Gly Gly Ile Arg Asp
                435                 440                 445

Gly Glu Glu Gly Gly Asp Thr Pro Leu Leu Ala Asn
    450                 455                 460
```

<210> SEQ ID NO 13
<211> LENGTH: 1441
<212> TYPE: DNA
<213> ORGANISM: Homo sapiens

<400> SEQUENCE: 13

| | | | | | |
|---|---|---|---|---|---|
| atggccacgc | tgcgccagct | gccgctctgc | accccatct | acaagctcct | actccccac | 60 |
| actcgataca | cgctgcaggt | gaacaccatc | gcgagggcca | cgctgctcaa | ccccgagggc | 120 |
| ctcgtggacc | aggtcacgtc | catcggggag | caaggcctca | tctacctcat | gagcacgggc | 180 |
| ctggcccact | tcacctacac | caatttctgc | cttccggaca | gcctgcgggc | ccgcggcgtc | 240 |
| ctggctatcc | ccaactacca | ctaccgagac | gacggcctga | gatctgggc | ggccattgag | 300 |
| agctttgtct | cagaaatcgt | gggctactat | tatcccagtg | acgcatctgt | gcagcaggat | 360 |
| tcggagctgc | aggcctggac | tggcgagatt | tttgctcagg | cgttcctggg | ccgggaaagc | 420 |
| tcaggtttcc | caagccggct | gtgcacccca | ggagagatgg | tgaagttcct | cactgcaatc | 480 |
| atcttcaatt | gctctgccca | gcacgctgct | gtcaacagtg | ggcagcatga | ctttggggcc | 540 |
| tggatgccca | atgctccatc | atccatgagg | cagcccccac | cccagaccaa | ggggaccacc | 600 |
| accctgaaga | cttacctaga | caccctccct | gaagtgaaca | tcagctgtaa | caacctcctc | 660 |
| ctcttctggt | tggttagcca | agaacccaag | gaccagagcc | ccctgggcac | ctacccagat | 720 |
| gagcacttca | cagaggaggc | cccgaggcgg | agcatcgccg | ccttccagag | ccgcctggcc | 780 |
| cagatctcaa | gggacatcca | ggagcggaac | cagggtctgg | cactgcccta | cacctacctg | 840 |
| gaccctcccc | tcattgagaa | cagcgtctcc | atctaaccac | ccccaaatac | cacccaagaa | 900 |
| gaaagaaagg | tccaagcatg | aggaggacca | gttcctcagg | tcctcagac | ccttccatcc | 960 |
| tccctgttct | cagttcacct | gaaccttctc | ttctgcacat | ggagactttt | gcagccaaga | 1020 |
| tggctctgac | atcatacaaa | ctgggccctg | agctgtgaga | gaccagcaca | gcagcgtcca | 1080 |
| ggttaaaagc | cgctgaccaa | agtccaatgc | acaatagccc | ctccgaaagg | aaggaaccgc | 1140 |
| ttcacttctt | gccccacttg | gggcagcctc | ttgttccagc | tcttggaat | gcccagcttg | 1200 |
| ggtttctgag | ctttctccc | tcatcctccc | caatccccaa | actccttctc | ctaccatgcc | 1260 |
| tttctacgtt | ctctttcttc | caagcctaga | gccaccagcc | cagcttcctt | ctctggaaaa | 1320 |
| gcctggaaac | tgggcacaga | aggactgtgt | gcctggctaa | catgtggtcc | cctttgtccc | 1380 |
| tagcaccttt | aaggggaggg | gaagaattgg | agggcagctt | gcctggaccc | ctaacggctg | 1440 |
| t | | | | | | 1441 |

<210> SEQ ID NO 14
<211> LENGTH: 291
<212> TYPE: PRT
<213> ORGANISM: Homo sapiens

<400> SEQUENCE: 14

Met Ala Thr Leu Arg Gln Leu Pro Leu Cys His Pro Ile Tyr Lys Leu
 1               5                  10                  15

Leu Leu Pro His Thr Arg Tyr Thr Leu Gln Val Asn Thr Ile Ala Arg
            20                  25                  30

Ala Thr Leu Leu Asn Pro Glu Gly Leu Val Asp Gln Val Thr Ser Ile
        35                  40                  45

Gly Arg Gln Gly Leu Ile Tyr Leu Met Ser Thr Gly Leu Ala His Phe
    50                  55                  60

```
Thr Tyr Thr Asn Phe Cys Leu Pro Asp Ser Leu Arg Ala Arg Gly Val
 65                  70                  75                  80

Leu Ala Ile Pro Asn Tyr His Tyr Arg Asp Asp Gly Leu Lys Ile Trp
                 85                  90                  95

Ala Ala Ile Glu Ser Phe Val Ser Glu Ile Val Gly Tyr Tyr Tyr Pro
            100                 105                 110

Ser Asp Ala Ser Val Gln Gln Asp Ser Glu Leu Gln Ala Trp Thr Gly
        115                 120                 125

Glu Ile Phe Ala Gln Ala Phe Leu Gly Arg Glu Ser Ser Gly Phe Pro
    130                 135                 140

Ser Arg Leu Cys Thr Pro Gly Glu Met Val Lys Phe Leu Thr Ala Ile
145                 150                 155                 160

Ile Phe Asn Cys Ser Ala Gln His Ala Ala Val Asn Ser Gly Gln His
                165                 170                 175

Asp Phe Gly Ala Trp Met Pro Asn Ala Pro Ser Ser Met Arg Gln Pro
            180                 185                 190

Pro Pro Gln Thr Lys Gly Thr Thr Leu Lys Thr Tyr Leu Asp Thr
        195                 200                 205

Leu Pro Glu Val Asn Ile Ser Cys Asn Asn Leu Leu Phe Trp Leu
    210                 215                 220

Val Ser Gln Glu Pro Lys Asp Gln Arg Pro Leu Gly Thr Tyr Pro Asp
225                 230                 235                 240

Glu His Phe Thr Glu Glu Ala Pro Arg Arg Ser Ile Ala Ala Phe Gln
                245                 250                 255

Ser Arg Leu Ala Gln Ile Ser Arg Asp Ile Gln Glu Arg Asn Gln Gly
            260                 265                 270

Leu Ala Leu Pro Tyr Thr Tyr Leu Asp Pro Pro Leu Ile Glu Asn Ser
        275                 280                 285

Val Ser Ile
    290

<210> SEQ ID NO 15
<211> LENGTH: 210
<212> TYPE: DNA
<213> ORGANISM: Homo sapiens

<400> SEQUENCE: 15
atggccacgc tgcgccagct gccgctctgc caccccatct acaagctcct actcccccac    60
actcgataca cgctgcaggt gaacaccatc gcgagggcca cgctgctcaa ccccgagggc   120
ctcgtggacc agcctgcggg cccgcggcgt cctggctatc ccaactacca ctaccgaga   180 cgacggcctg aagatctggg cggccattga                                    210

<210> SEQ ID NO 16
<211> LENGTH: 69
<212> TYPE: PRT
<213> ORGANISM: Homo sapiens

<400> SEQUENCE: 16

Met Ala Thr Leu Arg Gln Leu Pro Leu Cys His Pro Ile Tyr Lys Leu
  1               5                  10                  15

Leu Leu Pro His Thr Arg Tyr Thr Leu Gln Val Asn Thr Ile Ala Arg
             20                  25                  30

Ala Thr Leu Leu Asn Pro Glu Gly Leu Val Asp Gln Pro Ala Gly Pro
         35                  40                  45

Arg Arg Pro Gly Tyr Pro Gln Leu Pro Leu Pro Arg Arg Arg Pro Glu
```

```
                 50                  55                  60

Asp Leu Gly Gly His
 65

<210> SEQ ID NO 17
<211> LENGTH: 420
<212> TYPE: DNA
<213> ORGANISM: Homo sapiens

<400> SEQUENCE: 17
atggtgaagt tcctcactgc aatcatcttc aattgctctg cccagcacgc tgctgtcaac      60
agtgggcagc atgactttgg ggcctggatg cccaatgctc catcatccat gaggcagccc     120
ccacccagag ccaaggggac caccaccctg aagacttacc tagacacccc tcctgaagtg     180
aacatcagct gtaacaacct cctcctcttc tggttggtta gccaagaacc caaggaccag     240
aggcccctgg gcacctaccc agatgagcac ttcacagagg aggccccgag gcggagcatc     300
gccgccttcc agagccgcct ggcccagatc tcaagggaca tccaggagcg aaccagggt     360 ctggcactgc cctacaccta cctggaccct cccctcattg agaacagcgt ctccatctaa     420

<210> SEQ ID NO 18
<211> LENGTH: 139
<212> TYPE: PRT
<213> ORGANISM: Homo sapiens

<400> SEQUENCE: 18

Met Val Lys Phe Leu Thr Ala Ile Ile Phe Asn Cys Ser Ala Gln His
 1               5                  10                  15

Ala Ala Val Asn Ser Gly Gln His Asp Phe Gly Ala Trp Met Pro Asn
                20                  25                  30

Ala Pro Ser Ser Met Arg Gln Pro Pro Gln Thr Lys Gly Thr Thr
            35                  40                  45

Thr Leu Lys Thr Tyr Leu Asp Thr Leu Pro Glu Val Asn Ile Ser Cys
 50                  55                  60

Asn Asn Leu Leu Leu Phe Trp Leu Val Ser Gln Glu Pro Lys Asp Gln
 65                  70                  75                  80

Arg Pro Leu Gly Thr Tyr Pro Asp Glu His Phe Thr Glu Glu Ala Pro
                85                  90                  95

Arg Arg Ser Ile Ala Ala Phe Gln Ser Arg Leu Ala Gln Ile Ser Arg
            100                 105                 110

Asp Ile Gln Glu Arg Asn Gln Gly Leu Ala Leu Pro Tyr Thr Tyr Leu
        115                 120                 125

Asp Pro Pro Leu Ile Glu Asn Ser Val Ser Ile
    130                 135

<210> SEQ ID NO 19
<211> LENGTH: 588
<212> TYPE: DNA
<213> ORGANISM: Homo sapiens

<400> SEQUENCE: 19
atggccacgc tgcgccagct gccgctctgc cacccatct acaagctcct actcccccac      60
actcgataca cgctgcaggt gaacaccatc gcgagggcca cgctgctcaa ccccgagggc     120
ctcgtggacc aggtcacgtc catcgggagg caaggcctca tctacctcat gagcacgggc     180
ctggcccact tcacctacac caatttctgc cttccggaca gctgcgggc ccgcggcgtc     240 ctggctatcc ccaactacca ctaccgagac gacggcctga agatctgggc ggccattgag     300
```

```
agctttgtct cagaaatcgt gggctactat tatcccagtg acgcatctgt gcagcaggat      360
tcggagctgc aggcctggac tggcgagatt tttgctcagg cgttcctggg ccgggaaagc      420
tcaggtttcc caagccggct gtgcacccca ggagagatgg tgaagttcct cactgcaatc      480
atcttcaatt gctctgccca gcacgctgct gtcaacagtg ggcaggacgg cagaggtgga      540
atcagggatg gtgaagaggg aggtgatact cccttctgg ccaactga                    588
```

```
<210> SEQ ID NO 20
<211> LENGTH: 195
<212> TYPE: PRT
<213> ORGANISM: Homo sapiens

<400> SEQUENCE: 20
```

```
Met Ala Thr Leu Arg Gln Leu Pro Leu Cys His Pro Ile Tyr Lys Leu
 1               5                  10                  15

Leu Leu Pro His Thr Arg Tyr Thr Leu Gln Val Asn Thr Ile Ala Arg
                20                  25                  30

Ala Thr Leu Leu Asn Pro Glu Gly Leu Val Asp Gln Val Thr Ser Ile
            35                  40                  45

Gly Arg Gln Gly Leu Ile Tyr Leu Met Ser Thr Gly Leu Ala His Phe
        50                  55                  60

Thr Tyr Thr Asn Phe Cys Leu Pro Asp Ser Leu Arg Ala Arg Gly Val
65                  70                  75                  80

Leu Ala Ile Pro Asn Tyr His Tyr Arg Asp Asp Gly Leu Lys Ile Trp
                85                  90                  95

Ala Ala Ile Glu Ser Phe Val Ser Glu Ile Val Gly Tyr Tyr Tyr Pro
            100                 105                 110

Ser Asp Ala Ser Val Gln Gln Asp Ser Glu Leu Gln Ala Trp Thr Gly
        115                 120                 125

Glu Ile Phe Ala Gln Ala Phe Leu Gly Arg Glu Ser Ser Gly Phe Pro
    130                 135                 140

Ser Arg Leu Cys Thr Pro Gly Glu Met Val Lys Phe Leu Thr Ala Ile
145                 150                 155                 160

Ile Phe Asn Cys Ser Ala Gln His Ala Ala Val Asn Ser Gly Gln Asp
                165                 170                 175

Gly Arg Gly Gly Ile Arg Asp Gly Glu Glu Gly Asp Thr Pro Leu
            180                 185                 190

Leu Ala Asn
        195
```

```
<210> SEQ ID NO 21
<211> LENGTH: 898
<212> TYPE: DNA
<213> ORGANISM: Homo sapiens

<400> SEQUENCE: 21
atgcccaatg ctccatcatc catgaggcag ccccaccc agaccaaggg gaccaccacc        60
ctgaagactt acctagacac cctccctgaa gtgaacatca gctgtaacaa cctcctcctc     120
ttctggttgg ttagccaaga acccaaggac cagaggcccc tgggcaccta cccagatgag     180
cacttcacag aggaggcccc gaggcggagc atcgccgcct ccagagccg cctggcccag     240 atctcaaggg acatccagga gcggaaccag gtctggcac tgccctacac ctacctggac     300 cctccccctca ttgagaacag cgtctccatc taaccacccc caaataccac ccaagaagaa    360
agaaaggtcc aagcatgagg aggaccagtt cctcaggtcc tccagaccct ccatcctcc     420
```

```
ctgttctcag ttcacctgaa ccttctcttc tgcacatgga gacttttgca gccaagatgg      480
ctctgacatc atacaaactg ggccctgagc tgtgagagac cagcacagca gcgtccaggt      540
taaaagccgc tgaccaaagt ccaatgcaca atagcccctc cgaaaggaag gaaccgcttc      600
acttcttgcc ccacttgggg cagcctcttg ttccagcctc ttggaatgcc cagcttgggt      660
ttctgagctt ttctccctca tcctccccaa tccccaaact ccttctccta ccatgccttt      720
ctacgttctc tttcttccaa gcctagagcc accagcccag cttccttctc tggaaaagcc      780
tggaaactgg gcacagaagg actgtgtgcc tggctaacat gtggtcccct ttgtccctag      840
cacctttaag gggagggaa gaattggagg gcagcttgcc tggacccta acggctgt         898
```

<210> SEQ ID NO 22
<211> LENGTH: 110
<212> TYPE: PRT
<213> ORGANISM: Homo sapiens
<400> SEQUENCE: 22

```
Met Pro Asn Ala Pro Ser Ser Met Arg Gln Pro Pro Gln Thr Lys
 1               5                  10                  15

Gly Thr Thr Thr Leu Lys Thr Tyr Leu Asp Thr Leu Pro Glu Val Asn
                 20                  25                  30

Ile Ser Cys Asn Asn Leu Leu Leu Phe Trp Leu Val Ser Gln Glu Pro
             35                  40                  45

Lys Asp Gln Arg Pro Leu Gly Thr Tyr Pro Asp Glu His Phe Thr Glu
         50                  55                  60

Glu Ala Pro Arg Arg Ser Ile Ala Ala Phe Gln Ser Arg Leu Ala Gln
 65                  70                  75                  80

Ile Ser Arg Asp Ile Gln Glu Arg Asn Gln Gly Leu Ala Leu Pro Tyr
                 85                  90                  95

Thr Tyr Leu Asp Pro Pro Leu Ile Glu Asn Ser Val Ser Ile
                100                 105                 110
```

<210> SEQ ID NO 23
<211> LENGTH: 2604
<212> TYPE: DNA
<213> ORGANISM: Homo sapiens
<400> SEQUENCE: 23

```
atggggagga acagatcttg ggggacattg gggagtgggc ggacaagcac tccagggcat      60
cagtccgggc cgctgaccag gcggagggca gtgtcccaat tatacaggcg ttacctcctt     120
ttctccatct cagcatctga tccctccctc cgcagtggaa cccaggctcc tgatatccat     180
ctgggtgagc cagccagagg gaccggctgt gtcagaggca agcaaacaag tattagagtg     240
caagactgtg gcggagaga ggaagcccga gccgccagca gggagcttcg gagagagaaa     300
gcccaggaac atcccagaga gagctgggcc atcctcagc cctacccagc ccgcagccc      360 ctagccctcc gcccagaaac ccagccctgt ccggcgtgcc gctcttctcc tccaggccgg     420
ctgctgctgc ggcagcgtt gccggggcat cccttcctcc ttcccatcat ggcagtgtac     480
cgcctgtgtg tgaccactgg tccctacctg agggccggca cactggacaa catctctgtc     540
acactggtgg gcacgtgtgg tgaaagcccc aagcagcggc tagatcgaat gggcagggac     600
ttcgcccctg gatcggtaca gaagtacaag gtgcgttgca gcggagct gggtgagctc     660 ttgctgctgc gtgtacacaa ggagcgctac gctttcttcc gcaaggactc ttggtactgt     720
agccgcatct gtgtcaccga accggatggt agtgtatccc acttcccctg ctatcagtgg     780
```

-continued

```
attgaaggct actgcaccgt ggagctgagg ccaggaacag caagaactat ttgtcaggac      840
tctcttcccc tcctcctgga tcacaggaca cgggagctcc gggcccgaca agaatgctac      900
cgctggaaga tctatgcccc tggcttcccc tgcatggtag acgtcaacag ctttcaggag      960
atggagtcag acaagaaatt tgccttgaca agacgacaa cttgtgtaga ccagggtgac     1020
agcagtggga tcggtacct gcccggcttc cccatgaaaa ttgacatccc atccctgatg     1080
tacatggagc ccaatgttcg atactcagcc accaagacga tctcgctgct cttcaatgcc     1140
atccctgcgt ccttgggaat gaagcttcga gggctgttgg atcgcaaggg ctcctggaag     1200
aagctggatg acatgcagaa catcttctgg tgccataaga ccttcacgac aaagtatgtc     1260
acagagcact ggtgtgaaga tcacttcttt gggtaccagt acctgaatgg tgtcaatccc     1320
gtcatgctcc actgcatctc tagcttgccc agcaagctgc ctgtcaccaa tgacatggtg     1380 gccccttgc tgggacagga cacatgcctg cagacagagc tagagagggg gaacatcttc     1440
ctagcggact actggatcct ggcggaggcc cccacccact gcctaaacgg ccgccagcag     1500
tacgtggccg ccccactgtg cctgctgtgg ctcagccccc aggggcgct ggtgcccttg     1560 gccatccagc tcagccagac ccccgggcct gacagcccca tcttcctgcc cactgactcc     1620
gaatgggact ggctgctggc caagacgtgg gtgcgcaact ctgagttcct ggtgcacgaa     1680 acaacacgc actttctgtg cacgcatttg ctgtgcgagg ccttcgccat ggccacgctg     1740
cgccagctgc cgctctgcca ccccatctac aagctcctac tcccccacac tcgatacacg     1800
ctgcaggtga acaccatcgc gagggccacg ctgctcaacc ccgagggcct cgtggaccag     1860
gtcacgtcca tcgggaggca aggcctcatc tacctcatga gcacgggcct ggcccacttc     1920
acctacacca atttctgcct tccggacagc ctgcgggccc gcggcgtcct ggctatcccc     1980
aactaccact accgagacga cggcctgaag atctgggcgg ccattgagag ctttgtctca     2040
gaaatcgtgg gctactatta tcccagtgac gcatctgtgc agcaggattc ggagctgcag     2100
gcctggactg gcgagatttt tgctcaggcg ttcctgggcc gggaaagctc aggtttccca     2160
agccggctgt gcaccccagg agagatggtg aagttcctca ctgcaatcat cttcaattgc     2220
tctgcccagc acgctgctgt caacagtggg cagcatgact ttggggcctg gatgcccaat     2280
gctccatcat ccatgaggca gcccccaccc cagaccaagg ggaccaccac cctgaagact     2340
tacctagaca ccctccctga agtgaacatc agctgtaaca acctcctcct cttctggttg     2400
gttagccaag aacccaagga ccagaggccc ctgggcacct acccagatga gcacttcaca     2460
gaggaggccc cgaggcggag catcgccgcc ttccagagcc gcctggccca gatctcaagg     2520
gacatccagg agcggaacca gggtctggca ctgccctaca cctacctgga ccctcccctc     2580
attgagaaca gcgtctccat ctaa                                             2604
```

<210> SEQ ID NO 24
<211> LENGTH: 867
<212> TYPE: PRT
<213> ORGANISM: Homo sapiens

<400> SEQUENCE: 24

```
Met Gly Arg Asn Arg Ser Trp Gly Thr Leu Gly Ser Gly Arg Thr Ser
 1               5                  10                  15

Thr Pro Gly His Gln Ser Gly Pro Leu Thr Arg Arg Arg Ala Val Ser
            20                  25                  30

Gln Leu Tyr Arg Arg Tyr Leu Leu Phe Ser Ile Ser Ala Ser Asp Pro
        35                  40                  45
```

-continued

```
Ser Leu Arg Ser Gly Thr Gln Ala Pro Asp Ile His Leu Gly Glu Pro
    50                  55                  60

Ala Arg Gly Thr Gly Cys Val Arg Gly Lys Gln Thr Ser Ile Arg Val
65                  70                  75                  80

Gln Asp Cys Gly Arg Glu Glu Ala Arg Ala Ser Arg Glu Leu
                85                  90                  95

Arg Arg Glu Lys Ala Gln Glu His Pro Arg Glu Ser Trp Ala His Pro
            100                 105                 110

Gln Pro Tyr Pro Ala Pro Gln Pro Leu Ala Leu Arg Pro Glu Thr Gln
        115                 120                 125

Pro Cys Pro Ala Cys Arg Ser Ser Pro Gly Arg Leu Leu Leu Arg
    130                 135                 140

Pro Ala Leu Pro Gly His Pro Phe Leu Leu Pro Ile Met Ala Val Tyr
145                 150                 155                 160

Arg Leu Cys Val Thr Thr Gly Pro Tyr Leu Arg Ala Gly Thr Leu Asp
                165                 170                 175

Asn Ile Ser Val Thr Leu Val Gly Thr Cys Gly Glu Ser Pro Lys Gln
            180                 185                 190

Arg Leu Asp Arg Met Gly Arg Asp Phe Ala Pro Gly Ser Val Gln Lys
        195                 200                 205

Tyr Lys Val Arg Cys Thr Ala Glu Leu Gly Leu Leu Leu Leu Arg
    210                 215                 220

Val His Lys Glu Arg Tyr Ala Phe Phe Arg Lys Asp Ser Trp Tyr Cys
225                 230                 235                 240

Ser Arg Ile Cys Val Thr Glu Pro Asp Gly Ser Val Ser His Phe Pro
                245                 250                 255

Cys Tyr Gln Trp Ile Glu Gly Tyr Cys Thr Val Glu Leu Arg Pro Gly
            260                 265                 270

Thr Ala Arg Thr Ile Cys Gln Asp Ser Leu Pro Leu Leu Leu Asp His
        275                 280                 285

Arg Thr Arg Glu Leu Arg Ala Arg Gln Glu Cys Tyr Arg Trp Lys Ile
290                 295                 300

Tyr Ala Pro Gly Phe Pro Cys Met Val Asp Val Asn Ser Phe Gln Glu
305                 310                 315                 320

Met Glu Ser Asp Lys Lys Phe Ala Leu Thr Lys Thr Thr Cys Val
                325                 330                 335

Asp Gln Gly Asp Ser Ser Gly Asn Arg Tyr Leu Pro Gly Phe Pro Met
            340                 345                 350

Lys Ile Asp Ile Pro Ser Leu Met Tyr Met Glu Pro Asn Val Arg Tyr
        355                 360                 365

Ser Ala Thr Lys Thr Ile Ser Leu Leu Phe Asn Ala Ile Pro Ala Ser
    370                 375                 380

Leu Gly Met Lys Leu Arg Gly Leu Leu Asp Arg Lys Gly Ser Trp Lys
385                 390                 395                 400

Lys Leu Asp Asp Met Gln Asn Ile Phe Trp Cys His Lys Thr Phe Thr
                405                 410                 415

Thr Lys Tyr Val Thr Glu His Trp Cys Glu Asp His Phe Phe Gly Tyr
            420                 425                 430

Gln Tyr Leu Asn Gly Val Asn Pro Val Met Leu His Cys Ile Ser Ser
        435                 440                 445

Leu Pro Ser Lys Leu Pro Val Thr Asn Asp Met Val Ala Pro Leu Leu
450                 455                 460
```

```
Gly Gln Asp Thr Cys Leu Gln Thr Glu Leu Glu Arg Gly Asn Ile Phe
465                 470                 475                 480

Leu Ala Asp Tyr Trp Ile Leu Ala Glu Ala Pro Thr His Cys Leu Asn
            485                 490                 495

Gly Arg Gln Gln Tyr Val Ala Ala Pro Leu Cys Leu Leu Trp Leu Ser
        500                 505                 510

Pro Gln Gly Ala Leu Val Pro Leu Ala Ile Gln Leu Ser Gln Thr Pro
    515                 520                 525

Gly Pro Asp Ser Pro Ile Phe Leu Pro Thr Asp Ser Glu Trp Asp Trp
530                 535                 540

Leu Leu Ala Lys Thr Trp Val Arg Asn Ser Glu Phe Leu Val His Glu
545                 550                 555                 560

Asn Asn Thr His Phe Leu Cys Thr His Leu Leu Cys Glu Ala Phe Ala
                565                 570                 575

Met Ala Thr Leu Arg Gln Leu Pro Leu Cys His Pro Ile Tyr Lys Leu
            580                 585                 590

Leu Leu Pro His Thr Arg Tyr Thr Leu Gln Val Asn Thr Ile Ala Arg
        595                 600                 605

Ala Thr Leu Leu Asn Pro Glu Gly Leu Val Asp Gln Val Thr Ser Ile
    610                 615                 620

Gly Arg Gln Gly Leu Ile Tyr Leu Met Ser Thr Gly Leu Ala His Phe
625                 630                 635                 640

Thr Tyr Thr Asn Phe Cys Leu Pro Asp Ser Leu Arg Ala Arg Gly Val
                645                 650                 655

Leu Ala Ile Pro Asn Tyr His Tyr Arg Asp Asp Gly Leu Lys Ile Trp
            660                 665                 670

Ala Ala Ile Glu Ser Phe Val Ser Glu Ile Val Gly Tyr Tyr Tyr Pro
        675                 680                 685

Ser Asp Ala Ser Val Gln Gln Asp Ser Glu Leu Gln Ala Trp Thr Gly
690                 695                 700

Glu Ile Phe Ala Gln Ala Phe Leu Gly Arg Glu Ser Ser Gly Phe Pro
705                 710                 715                 720

Ser Arg Leu Cys Thr Pro Gly Glu Met Val Lys Phe Leu Thr Ala Ile
                725                 730                 735

Ile Phe Asn Cys Ser Ala Gln His Ala Ala Val Asn Ser Gly Gln His
            740                 745                 750

Asp Phe Gly Ala Trp Met Pro Asn Ala Pro Ser Ser Met Arg Gln Pro
        755                 760                 765

Pro Pro Gln Thr Lys Gly Thr Thr Leu Lys Thr Tyr Leu Asp Thr
770                 775                 780

Leu Pro Glu Val Asn Ile Ser Cys Asn Asn Leu Leu Leu Phe Trp Leu
785                 790                 795                 800

Val Ser Gln Glu Pro Lys Asp Gln Arg Pro Leu Gly Thr Tyr Pro Asp
                805                 810                 815

Glu His Phe Thr Glu Glu Ala Pro Arg Arg Ser Ile Ala Ala Phe Gln
            820                 825                 830

Ser Arg Leu Ala Gln Ile Ser Arg Asp Ile Glu Arg Asn Gln Gly
        835                 840                 845

Leu Ala Leu Pro Tyr Thr Tyr Leu Asp Pro Pro Leu Ile Glu Asn Ser
850                 855                 860

Val Ser Ile
865
```

<210> SEQ ID NO 25
<211> LENGTH: 1938
<212> TYPE: DNA
<213> ORGANISM: Homo sapiens

<400> SEQUENCE: 25

| | |
|---|---|
| atgggagga acagatcttg ggggacattg gggagtgggc ggacaagcac tccagggcat | 60 |
| cagtccgggc cgctgaccag gcggagggca gtgtcccaat tatacaggcg ttacctcctt | 120 |
| ttctccatct cagcatctga tccctccctc cgcagtggaa cccaggctcc tgatatccat | 180 |
| ctgggtgagc cagccagagg gaccggctgt gtcagaggca agcaaacaag tattagagtg | 240 |
| caagactgtg ggcggagaga ggaagcccga ccgccagca gggagcttcg gagagagaaa | 300 |
| gcccaggaac atcccagaga gagctgggcc atcctcagc cctacccagc ccgcagccc | 360 |
| ctagccctcc gcccagaaac ccagccctgt ccggcgtgcc gctcttctcc tccaggccgg | 420 |
| ctgctgctgc ggccagcgtt gccggggcat cccttcctcc ttcccatcat ggcagtgtac | 480 |
| cgcctgtgtg tgaccactgg tccctacctg agggccggca cactggacaa catctctgtc | 540 |
| acactggtgg gcacgtgtgg tgaaagcccc aagcagcggc tagatcgaat gggcagggac | 600 |
| ttcgccctg gatcggtaca aagtacaag gtgcgttgca gcggagct gggtgagctc | 660 |
| ttgctgctgc gtgtacacaa ggagcgctac gctttcttcc gcaaggactc ttggtactgt | 720 |
| agccgcatct gtgtcaccga accggatggt agtgtatccc acttccctg ctatcagtgg | 780 |
| attgaaggct actgcaccgt ggagctgagg ccaggaacag caagaactat tgtcaggac | 840 |
| tctcttcccc tcctcctgga tcacaggaca cgggagctcc gggcccgaca gaatgctac | 900 |
| cgctggaaga tctatgcccc tggcttcccc tgcatggtag acgtcaacag ctttcaggag | 960 |
| atggagtcag acaagaaatt tgccttgaca agacgacaa cttgtgtaga ccagggtgac | 1020 |
| agcagtggga atcggtacct gcccggcttc cccatgaaaa ttgacatccc atccctgatg | 1080 |
| tacatggagc ccaatgttcg atactcagcc accaagacga tctcgctgct cttcaatgcc | 1140 |
| atccctgcgt ccttgggaat gaagcttcga gggctgttgg atcgcaaggg ctcctggaag | 1200 |
| aagctggatg acatgcagaa catcttctgg tgccataaga ccttcacgac aaagtatgtc | 1260 |
| acagagcact ggtgtgaaga tcacttcttt gggtaccagt acctgaatgg tgtcaatccc | 1320 |
| gtcatgctcc actgcatctc tagcttgccc agcaagctgc ctgtcaccaa tgacatggtg | 1380 |
| gccccttgc tgggacagga cacatgcctg cagacagagc tagagagggg gaacatcttc | 1440 |
| ctagcggact actggatcct ggcggaggcc ccacccact gcctaaacgg ccgccagcag | 1500 |
| tacgtggccg ccccactgtg cctgctgtgg ctcagccccc aggggcgct ggtgcccttg | 1560 |
| gccatccagc tcagccagac ccccgggcct gacagcccca tcttcctgcc cactgactcc | 1620 |
| gaatgggact ggctgctggc caagacgtgg gtgcgcaact ctgagttcct ggtgcacgaa | 1680 |
| aacaacacgc actttctgtg cacgcatttg ctgtgcgagg ccttcgccat ggccacgctg | 1740 |
| cgccagctgc cgctctgcca ccccatctac aagctcctac tcccccacac tcgatacacg | 1800 |
| ctgcaggtga acaccatcgc gagggccacg ctgctcaacc cgagggcct cgtggaccag | 1860 |
| cctgcgggcc cgcggcgtcc tggctatccc caactaccac taccgagacg acggcctgaa | 1920 |
| gatctgggcg gccattga | 1938 |

<210> SEQ ID NO 26
<211> LENGTH: 645
<212> TYPE: PRT
<213> ORGANISM: Homo sapiens

<400> SEQUENCE: 26

```
Met Gly Arg Asn Arg Ser Trp Gly Thr Leu Gly Ser Gly Arg Thr Ser
1               5                   10                  15

Thr Pro Gly His Gln Ser Gly Pro Leu Thr Arg Arg Arg Ala Val Ser
            20                  25                  30

Gln Leu Tyr Arg Arg Tyr Leu Leu Phe Ser Ile Ser Ala Ser Asp Pro
        35                  40                  45

Ser Leu Arg Ser Gly Thr Gln Ala Pro Asp Ile His Leu Gly Glu Pro
    50                  55                  60

Ala Arg Gly Thr Gly Cys Val Arg Gly Lys Gln Thr Ser Ile Arg Val
65                  70                  75                  80

Gln Asp Cys Gly Arg Arg Glu Glu Ala Arg Ala Ser Arg Glu Leu
                85                  90                  95

Arg Arg Glu Lys Ala Gln Glu His Pro Arg Glu Ser Trp Ala His Pro
                100                 105                 110

Gln Pro Tyr Pro Ala Pro Gln Pro Leu Ala Leu Arg Pro Glu Thr Gln
            115                 120                 125

Pro Cys Pro Ala Cys Arg Ser Ser Pro Pro Gly Arg Leu Leu Leu Arg
130                 135                 140

Pro Ala Leu Pro Gly His Pro Phe Leu Leu Pro Ile Met Ala Val Tyr
145                 150                 155                 160

Arg Leu Cys Val Thr Thr Gly Pro Tyr Leu Arg Ala Gly Thr Leu Asp
                165                 170                 175

Asn Ile Ser Val Thr Leu Val Gly Thr Cys Gly Glu Ser Pro Lys Gln
            180                 185                 190

Arg Leu Asp Arg Met Gly Arg Asp Phe Ala Pro Gly Ser Val Gln Lys
        195                 200                 205

Tyr Lys Val Arg Cys Thr Ala Glu Leu Gly Glu Leu Leu Leu Arg
210                 215                 220

Val His Lys Glu Arg Tyr Ala Phe Phe Arg Lys Asp Ser Trp Tyr Cys
225                 230                 235                 240

Ser Arg Ile Cys Val Thr Glu Pro Asp Gly Ser Val Ser His Phe Pro
                245                 250                 255

Cys Tyr Gln Trp Ile Glu Gly Tyr Cys Thr Val Glu Leu Arg Pro Gly
            260                 265                 270

Thr Ala Arg Thr Ile Cys Gln Asp Ser Leu Pro Leu Leu Leu Asp His
275                 280                 285

Arg Thr Arg Glu Leu Arg Ala Arg Gln Glu Cys Tyr Arg Trp Lys Ile
290                 295                 300

Tyr Ala Pro Gly Phe Pro Cys Met Val Asp Val Asn Ser Phe Gln Glu
305                 310                 315                 320

Met Glu Ser Asp Lys Lys Phe Ala Leu Thr Lys Thr Thr Cys Val
                325                 330                 335

Asp Gln Gly Asp Ser Ser Gly Asn Arg Tyr Leu Pro Gly Phe Pro Met
            340                 345                 350

Lys Ile Asp Ile Pro Ser Leu Met Tyr Met Glu Pro Asn Val Arg Tyr
        355                 360                 365

Ser Ala Thr Lys Thr Ile Ser Leu Leu Phe Asn Ala Ile Pro Ala Ser
    370                 375                 380

Leu Gly Met Lys Leu Arg Gly Leu Leu Asp Arg Lys Gly Ser Trp Lys
385                 390                 395                 400

Lys Leu Asp Asp Met Gln Asn Ile Phe Trp Cys His Lys Thr Phe Thr
                405                 410                 415
```

Thr Lys Tyr Val Thr Glu His Trp Cys Glu Asp His Phe Phe Gly Tyr
            420                 425                 430

Gln Tyr Leu Asn Gly Val Asn Pro Val Met Leu His Cys Ile Ser Ser
            435                 440                 445

Leu Pro Ser Lys Leu Pro Val Thr Asn Asp Met Val Ala Pro Leu Leu
        450                 455                 460

Gly Gln Asp Thr Cys Leu Gln Thr Glu Leu Glu Arg Gly Asn Ile Phe
465                 470                 475                 480

Leu Ala Asp Tyr Trp Ile Leu Ala Glu Ala Pro Thr His Cys Leu Asn
                485                 490                 495

Gly Arg Gln Gln Tyr Val Ala Ala Pro Leu Cys Leu Leu Trp Leu Ser
            500                 505                 510

Pro Gln Gly Ala Leu Val Pro Leu Ala Ile Gln Leu Ser Gln Thr Pro
            515                 520                 525

Gly Pro Asp Ser Pro Ile Phe Leu Pro Thr Asp Ser Glu Trp Asp Trp
        530                 535                 540

Leu Leu Ala Lys Thr Trp Val Arg Asn Ser Glu Phe Leu Val His Glu
545                 550                 555                 560

Asn Asn Thr His Phe Leu Cys Thr His Leu Leu Cys Glu Ala Phe Ala
                565                 570                 575

Met Ala Thr Leu Arg Gln Leu Pro Leu Cys His Pro Ile Tyr Lys Leu
            580                 585                 590

Leu Leu Pro His Thr Arg Tyr Thr Leu Gln Val Asn Thr Ile Ala Arg
            595                 600                 605

Ala Thr Leu Leu Asn Pro Glu Gly Leu Val Asp Gln Pro Ala Gly Pro
        610                 615                 620

Arg Arg Pro Gly Tyr Pro Gln Leu Pro Leu Pro Arg Arg Arg Pro Glu
625                 630                 635                 640

Asp Leu Gly Gly His
            645

<210> SEQ ID NO 27
<211> LENGTH: 2316
<212> TYPE: DNA
<213> ORGANISM: Homo sapiens

<400> SEQUENCE: 27
atggggagga acagatcttg ggggacattg gggagtgggc ggacaagcac tccagggcat     60
cagtccgggc cgctgaccag gcggagggca gtgtcccaat tatacaggcg ttacctcctt    120
ttctccatct cagcatctga tccctccctc cgcagtggaa cccaggctcc tgatatccat    180
ctgggtgagc cagccagagg gaccggctgt gtcagaggca agcaaacaag tattagagtg    240
caagactgtg gcggagagag gaagcccga gccgccagca gggagcttcg gagagagaaa     300
gcccaggaac atcccagaga gagctgggcc atcctcagcc ctacccagcc ccgcagcccc    360
ctagccctcc gcccagaaac ccagccctgt ccggcgtgcc gctcttctcc tccaggccgg    420
ctgctgctgc ggccagcgtt gccggggcat cccttcctcc ttcccatcat ggcagtgtac    480
cgcctgtgtg tgaccactgg tccctacctg agggccggca cactggacaa catctctgtc    540
acactggtgg gcacgtgtgg tgaaagcccc aagcagcggc tagatcgaat gggcagggac    600
ttcgcccctg atcggtacag aagtacaagg gtgcgttgca cagcggagct gggtgagctc    660
ttgctgctgc gtgtacacaa ggagcgctac gctttcttcc gcaaggactc ttggtactgt    720
agccgcatct gtgtcaccga accggatggt agtgtatccc acttcccctg ctatcagtgg    780

-continued

```
attgaaggct actgcaccgt ggagctgagg ccaggaacag caagaactat ttgtcaggac    840
tctcttcccc tcctcctgga tcacaggaca cgggagctcc gggcccgaca gaatgctac     900 cgctggaaga tctatgcccc tggcttcccc tgcatggtag acgtcaacag ctttcaggag    960
atggagtcag acaagaaatt tgccttgaca agacgacaa  cttgtgtaga ccagggtgac   1020
agcagtggga tcggtacct  gcccggcttc cccatgaaaa ttgacatccc atccctgatg   1080
tacatggagc ccaatgttcg atactcagcc accaagacga tctcgctgct cttcaatgcc   1140
atccctgcgt ccttgggaat gaagcttcga gggctgttgg atcgcaaggg ctcctggaag   1200
aagctggatg acatgcagaa catcttctgg tgccataaga ccttcacgac aaagtatgtc   1260
acagagcact ggtgtgaaga tcacttcttt gggtaccagt acctgaatgg tgtcaatccc   1320
gtcatgctcc actgcatctc tagcttgccc agcaagctgc ctgtcaccaa tgacatggtg   1380 gccccttgc  tgggacagga cacatgcctg cagacagagc tagagagggg gaacatcttc   1440
ctagcggact actggatcct ggcggaggcc cccacccact gcctaaacgg ccgccagcag   1500
tacgtggccg ccccactgtg cctgctgtgg ctcagccccc aggggcgct  ggtgcccttg   1560 gccatccagc tcagccagac ccccgggcct gacagcccca tcttcctgcc cactgactcc   1620
gaatgggact ggctgctggc caagacgtgg gtgcgcaact ctgagttcct ggtgcacgaa   1680
aacaacacgc actttctgtg cacgcatttg ctgtgcgagg ccttcgccat ggccacgctg   1740
cgccagctgc cgctctgcca ccccatctac aagctcctac tcccccacac tcgatacacg   1800
ctgcaggtga acaccatcgc gagggccacg ctgctcaacc ccgagggcct cgtggaccag   1860
gtcacgtcca tcgggaggca aggcctcatc tacctcatga gcacgggcct ggcccacttc   1920
acctacacca atttctgcct tccggacagc ctgcgggccc gcggcgtcct ggctatcccc   1980
aactaccact accgagacga cggcctgaag atctgggcgg ccattgagag ctttgtctca   2040
gaaatcgtgg gctactatta tcccagtgac gcatctgtgc agcaggattc ggagctgcag   2100
gcctggactg gcgagatttt tgctcaggcg ttcctgggcc gggaaagctc aggtttccca   2160
agccggctgt gcaccccagg agagatggtg aagttcctca ctgcaatcat cttcaattgc   2220
tctgcccagc acgctgctgt caacagtggg caggacggca gaggtggaat cagggatggt   2280
gaagagggag gtgatactcc ccttctggcc aactga                             2316
```

<210> SEQ ID NO 28
<211> LENGTH: 771
<212> TYPE: PRT
<213> ORGANISM: Homo sapiens

<400> SEQUENCE: 28

```
Met Gly Arg Asn Arg Ser Trp Gly Thr Leu Gly Ser Gly Arg Thr Ser
  1               5                  10                  15

Thr Pro Gly His Gln Ser Gly Pro Leu Thr Arg Arg Ala Val Ser
             20                  25                  30

Gln Leu Tyr Arg Arg Tyr Leu Leu Phe Ser Ile Ser Ala Ser Asp Pro
         35                  40                  45

Ser Leu Arg Ser Gly Thr Gln Ala Pro Asp Ile His Leu Gly Glu Pro
     50                  55                  60

Ala Arg Gly Thr Gly Cys Val Arg Gly Lys Thr Ser Ile Arg Val
 65                  70                  75                  80

Gln Asp Cys Gly Arg Arg Glu Glu Ala Arg Ala Ser Arg Glu Leu
                 85                  90                  95
```

-continued

```
Arg Arg Glu Lys Ala Gln Glu His Pro Arg Glu Ser Trp Ala His Pro
            100                 105                 110
Gln Pro Tyr Pro Ala Pro Gln Pro Leu Ala Leu Arg Pro Glu Thr Gln
        115                 120                 125
Pro Cys Pro Ala Cys Arg Ser Ser Pro Pro Gly Arg Leu Leu Leu Arg
    130                 135                 140
Pro Ala Leu Pro Gly His Pro Phe Leu Pro Ile Met Ala Val Tyr
145                 150                 155                 160
Arg Leu Cys Val Thr Thr Gly Pro Tyr Leu Arg Ala Gly Thr Leu Asp
                165                 170                 175
Asn Ile Ser Val Thr Leu Val Gly Thr Cys Gly Glu Ser Pro Lys Gln
            180                 185                 190
Arg Leu Asp Arg Met Gly Arg Asp Phe Ala Pro Gly Ser Val Gln Lys
        195                 200                 205
Tyr Lys Val Arg Cys Thr Ala Glu Leu Gly Glu Leu Leu Leu Arg
    210                 215                 220
Val His Lys Glu Arg Tyr Ala Phe Phe Arg Lys Asp Ser Trp Tyr Cys
225                 230                 235                 240
Ser Arg Ile Cys Val Thr Glu Pro Asp Gly Ser Val Ser His Phe Pro
                245                 250                 255
Cys Tyr Gln Trp Ile Glu Gly Tyr Cys Thr Val Glu Leu Arg Pro Gly
            260                 265                 270
Thr Ala Arg Thr Ile Cys Gln Asp Ser Leu Pro Leu Leu Asp His
        275                 280                 285
Arg Thr Arg Glu Leu Arg Ala Arg Gln Glu Cys Tyr Arg Trp Lys Ile
    290                 295                 300
Tyr Ala Pro Gly Phe Pro Cys Met Val Asp Val Asn Ser Phe Gln Glu
305                 310                 315                 320
Met Glu Ser Asp Lys Lys Phe Ala Leu Thr Lys Thr Thr Cys Val
                325                 330                 335
Asp Gln Gly Asp Ser Ser Gly Asn Arg Tyr Leu Pro Gly Phe Pro Met
            340                 345                 350
Lys Ile Asp Ile Pro Ser Leu Met Tyr Met Glu Pro Asn Val Arg Tyr
        355                 360                 365
Ser Ala Thr Lys Thr Ile Ser Leu Leu Phe Asn Ala Ile Pro Ala Ser
    370                 375                 380
Leu Gly Met Lys Leu Arg Gly Leu Leu Asp Arg Lys Gly Ser Trp Lys
385                 390                 395                 400
Lys Leu Asp Asp Met Gln Asn Ile Phe Trp Cys His Lys Thr Phe Thr
                405                 410                 415
Thr Lys Tyr Val Thr Glu His Trp Cys Glu Asp His Phe Phe Gly Tyr
            420                 425                 430
Gln Tyr Leu Asn Gly Val Asn Pro Val Met Leu His Cys Ile Ser Ser
        435                 440                 445
Leu Pro Ser Lys Leu Pro Val Thr Asn Asp Met Val Ala Pro Leu Leu
    450                 455                 460
Gly Gln Asp Thr Cys Leu Gln Thr Glu Leu Glu Arg Gly Asn Ile Phe
465                 470                 475                 480
Leu Ala Asp Tyr Trp Ile Leu Ala Glu Ala Pro Thr His Cys Leu Asn
                485                 490                 495
Gly Arg Gln Gln Tyr Val Ala Ala Pro Leu Cys Leu Leu Trp Leu Ser
            500                 505                 510
Pro Gln Gly Ala Leu Val Pro Leu Ala Ile Gln Leu Ser Gln Thr Pro
```

```
                515                 520                 525
Gly Pro Asp Ser Pro Ile Phe Leu Pro Thr Asp Ser Glu Trp Asp Trp
        530                 535                 540

Leu Leu Ala Lys Thr Trp Val Arg Asn Ser Glu Phe Leu Val His Glu
545                 550                 555                 560

Asn Asn Thr His Phe Leu Cys Thr His Leu Leu Cys Glu Ala Phe Ala
                565                 570                 575

Met Ala Thr Leu Arg Gln Leu Pro Leu Cys His Pro Ile Tyr Lys Leu
            580                 585                 590

Leu Leu Pro His Thr Arg Tyr Thr Leu Gln Val Asn Thr Ile Ala Arg
        595                 600                 605

Ala Thr Leu Leu Asn Pro Glu Gly Leu Val Asp Gln Val Thr Ser Ile
    610                 615                 620

Gly Arg Gln Gly Leu Ile Tyr Leu Met Ser Thr Gly Leu Ala His Phe
625                 630                 635                 640

Thr Tyr Thr Asn Phe Cys Leu Pro Asp Ser Leu Arg Ala Arg Gly Val
                645                 650                 655

Leu Ala Ile Pro Asn Tyr His Tyr Arg Asp Asp Gly Leu Lys Ile Trp
            660                 665                 670

Ala Ala Ile Glu Ser Phe Val Ser Glu Ile Val Gly Tyr Tyr Tyr Pro
        675                 680                 685

Ser Asp Ala Ser Val Gln Gln Asp Ser Glu Leu Gln Ala Trp Thr Gly
    690                 695                 700

Glu Ile Phe Ala Gln Ala Phe Leu Gly Arg Glu Ser Ser Gly Phe Pro
705                 710                 715                 720

Ser Arg Leu Cys Thr Pro Gly Glu Met Val Lys Phe Leu Thr Ala Ile
                725                 730                 735

Ile Phe Asn Cys Ser Ala Gln His Ala Ala Val Asn Ser Gly Gln Asp
            740                 745                 750

Gly Arg Gly Gly Ile Arg Asp Gly Glu Glu Gly Asp Thr Pro Leu
        755                 760                 765

Leu Ala Asn
    770

<210> SEQ ID NO 29
<211> LENGTH: 3384
<212> TYPE: DNA
<213> ORGANISM: Homo sapiens

<400> SEQUENCE: 29
caggtgccct gtgctcatct ctgcctggga atggggagga acagatcttg ggggacattg       60
gggagtgggc ggacaagcac tccagggcat cagtccgggc cgctgaccag gcggagggca      120
gtgtcccaat tatacaggcg ttacctcctt ttctccatct cagcatctga tccctccctc      180
cgcagtggaa cccaggctcc tgatatccat ctgggtgagc cagccagagg gaccggctgt      240
gtcagaggca agcaaacaag tattagagtg caagactgtg ggcggagaga ggaagcccga      300
gccgccagca gggagcttcg gagagagaaa gcccaggaac atcccagaga gagctgggcc      360
catcctcagc cctacccagc cccgcagccc ctagccctcc gcccagaaac ccagccctgt      420
ccggcgtgcc gctcttctcc tccaggccgg ctgctgctgc ggccagcgtt gccgggcat       480 cccttcctcc ttcccatcat ggcagtgtac cgcctgtgtg tgaccactgg tcctacctg       540 agggccggca cactggacaa catctctgtc acactggtgg gcacgtgtgg tgaaagcccc      600
aagcagcggc tagatcgaat gggcagggac ttcgcccctg gatcggtaca gaagtacaag      660
```

-continued

```
gtgcgttgca cagcggagct gggtgagctc ttgctgctgc gtgtacacaa ggagcgctac      720
gctttcttcc gcaaggactc ttggtactgt agccgcatct gtgtcaccga accggatggt      780
agtgtatccc acttcccctg ctatcagtgg attgaaggct actgcaccgt ggagctgagg      840
ccaggaacag caagaactat tgtcaggac tctcttcccc tcctcctgga tcacaggaca       900
cgggagctcc gggcccgaca agaatgctac cgctggaaga tctatgcccc tggcttcccc      960
tgcatggtag acgtcaacag ctttcaggag atggagtcag acaagaaatt tgccttgaca     1020
aagacgacaa cttgtgtaga ccagggtgac agcagtggga tcggtacct gcccggcttc      1080
cccatgaaaa ttgacatccc atccctgatg tacatggagc ccaatgttcg atactcagcc     1140
accaagacga tctcgctgct cttcaatgcc atccctgcgt ccttgggaat gaagcttcga     1200
gggctgttgg atcgcaaggg ctcctggaag aagctggatg acatgcagaa catcttctgg     1260
tgccataaga ccttcacgac aaagtatgtc acagagcact ggtgtgaaga tcacttcttt     1320
gggtaccagt acctgaatgg tgtcaatccc gtcatgctcc actgcatctc tagcttgccc     1380
agcaagctgc ctgtcaccaa tgacatggtg gccccttgc tgggacagga cacatgcctg      1440
cagacagagc tagagagggg gaacatcttc ctagcggact actggatcct ggcggaggcc     1500
cccaccccact gcctaaacgg ccgccagcag tacgtggccg ccccactgtg cctgctgtgg     1560
ctcagccccc aggggcgct ggtgcccttg gccatccagc tcagccagac ccccgggcct      1620
gacagcccca tcttcctgcc cactgactcc gaatgggact ggctgctggc caagacgtgg     1680
gtgcgcaact ctgagttcct ggtgcacgaa acaacacgc actttctgtg cacgcatttg      1740
ctgtgcgagg ccttcgccat ggccacgctg cgccagctgc cgctctgcca ccccatctac     1800
aagctcctac tcccccacac tcgatacacg ctgcaggtga acaccatcgc gagggccacg     1860
ctgctcaacc ccgagggcct cgtggaccag gtcacgtcca tcgggaggca aggcctcatc     1920
tacctcatga gcacgggcct ggcccacttc acctaccacca atttctgcct tccgacagc     1980
ctgcgggccc gcggcgtcct ggctatcccc aactaccact accgagacga cggcctgaag     2040
atctgggcgg ccattgagag cttttgtctca gaaatcgtgg gctactatta tcccagtgac     2100
gcatctgtgc agcaggattc ggagctgcag gcctggactg gcgagatttt tgctcaggcg     2160
ttcctgggcc gggaaagctc aggtttccca agccggctgt gcaccccagg agagatggtg     2220
aagttcctca ctgcaatcat cttcaattgc tctgcccagc acgctgctgt caacagtggg     2280
cagcatgact ttggggcctg gatgcccaat gctccatcat ccatgaggca gccccaccc      2340
cagaccaagg ggaccaccac cctgaagact tacctagaca ccctccctga agtgaacatc     2400
agctgtaaca acctcctcct cttctggttg gttagccaag aacccaagga ccagaggccc     2460
ctgggcacct acccagatga gcacttcaca gaggaggccc cgaggcggag catcgccgcc     2520
ttccagagcc gcctggccca gatctcaagg gacatccagg agcggaacca gggtctggca     2580
ctgccctaca cctacctgga ccctccctc attgagaaca gtgtctccat ctaaccaccc     2640
ccaaatacca cccaagaaga aagaaaggtc caagcatgag gaggaccagt tcctcaggtc     2700
ctccagaccc ttccatcctc cctgttctca gttcacctga accttctctt ctgcacatgg     2760
agactttgc agccaagatg gctctgacat catacaaact gggccctgag ctgtgagaga      2820
ccagcacagc agcgtccagg ttaaaagccg ctgaccaaag tccaatgcac aatagcccct     2880
ccgaaaggaa ggaaccgctt cacttcttgc cccacttggg gcagcctctt gttccagcct     2940
cttggaatgc ccagcttggg tttctgagct tttctccctc atcctccccc atccccaaac     3000
```

-continued

| | | | | | |
|---|---|---|---|---|---|
| tccttctcct | accatgcctt | tctacgttct | ctttcttcca | agcctagagc | caccagccca | 3060 |
| gcttccttct | ctggaaaagc | ctggaaactg | ggcacagaag | gactgtgtgc | ctgggtctaa | 3120 |
| catgtggtcc | cctttgtccc | tagcaccttt | aaggggaggg | gaagaattgg | agggcagctt | 3180 |
| gcctggaccc | ctaacggctg | ttctcaggaa | caggttccca | ggcctggggt | gtttgtggag | 3240 |
| atctgtcttt | ctccaaagat | ttcatccaac | tcccctttca | tcccactccc | tttcatccca | 3300 |
| tttttttctt | tctgtccttg | agcccagtga | gttcaataaa | aaccaaaata | tttggcaaaa | 3360 |
| aaaaaaaaaa | aaaaaaaaaa | aaaa | | | | 3384 |